United States Patent
Della Rocca et al.

(10) Patent No.: US 8,364,258 B2
(45) Date of Patent: Jan. 29, 2013

(54) DEVICE, METHOD, AND SYSTEM FOR NEURAL MODULATION AS VACCINE ADJUVANT IN A VERTEBRATE SUBJECT

(75) Inventors: Gregory J. Della Rocca, Columbia, MO (US); Joshua L. Dowling, Webster Groves, MO (US); Eleanor V. Goodall, Seattle, WA (US); Roderick A. Hyde, Redmond, WA (US); Jordin T. Kare, Seattle, WA (US); Muriel Y. Ishikawa, Livermore, CA (US); Eric C. Leuthardt, St. Louis, MO (US); Stephen L. Malaska, Redmond, WA (US); Nathan P. Myhrvold, Bellevue, WA (US); Paul Santiago, St. Louis, MO (US); Todd J. Stewart, St. Louis, MO (US); Elizabeth A. Sweeney, Seattle, WA (US); Clarence T. Tegreene, Bellevue, WA (US); Lowell L. Wood, Jr., Bellevue, WA (US); Victoria Y. H. Wood, Livermore, CA (US)

(73) Assignee: The Invention Science Fund I, LLC, Bellevue, WA (US)

( * ) Notice: Subject to any disclaimer, the term of this patent is extended or adjusted under 35 U.S.C. 154(b) by 248 days.

(21) Appl. No.: 12/802,812

(22) Filed: Jun. 14, 2010

(65) Prior Publication Data

US 2011/0152748 A1    Jun. 23, 2011

Related U.S. Application Data

(63) Continuation of application No. 12/655,195, filed on Dec. 22, 2009.

(51) Int. Cl.
*A61N 1/18* (2006.01)

(52) U.S. Cl. .................................. 607/3; 607/45; 607/2

(58) Field of Classification Search .................. 607/2–3, 607/45

See application file for complete search history.

(56) References Cited

U.S. PATENT DOCUMENTS

| 4,891,219 | A |  1/1990 | Karr, Jr. et al. |
| 5,476,438 | A | 12/1995 | Edrich et al. |
| 5,945,508 | A |  8/1999 | Witten et al. |
| 5,998,376 | A | 12/1999 | Witten et al. |
| 6,572,866 | B1 |  6/2003 | Torcia |
| 6,610,713 | B2 |  8/2003 | Tracey |
| 6,819,958 | B2 | 11/2004 | Weiner et al. |
| 7,141,034 | B2 * | 11/2006 | Eppstein et al. ............... 604/22 |
| 7,149,574 | B2 | 12/2006 | Yun et al. |

(Continued)

FOREIGN PATENT DOCUMENTS

| EP | 0957930 B1 | 3/2004 |
| WO | WO 2005/014105 A1 | 2/2005 |

(Continued)

OTHER PUBLICATIONS

Singer, Emily; "Neural Stimulation for Autoimmune Diseases"; Technology Review; bearing a date of Jun. 1, 2010; pp. 1-2; MIT.

(Continued)

*Primary Examiner* — Carl H Layno
*Assistant Examiner* — Paula J Stice

(57) ABSTRACT

An apparatus for enhancing an immune response in a vertebrate subject is described. The apparatus includes providing at least one energy stimulus configured to modulate one or more nervous system components of the vertebrate subject, and administering one or more immunogen to the vertebrate subject, wherein the at least one energy stimulus and the one or more immunogen are provided in a combination and in a temporal sequence sufficient to enhance an immune response in the vertebrate subject.

38 Claims, 5 Drawing Sheets

U.S. PATENT DOCUMENTS

| | | | |
|---|---|---|---|
| 7,155,278 | B2 | 12/2006 | King et al. |
| 7,244,438 | B2 | 7/2007 | Lingnau et al. |
| 7,321,793 | B2 | 1/2008 | Ben Ezra et al. |
| 7,418,292 | B2 * | 8/2008 | Shafer .............................. 607/2 |
| 7,444,183 | B2 | 10/2008 | Knudson et al. |
| 7,700,111 | B2 | 4/2010 | Miller et al. |
| 2002/0127234 | A1 * | 9/2002 | El Halawani et al. ...... 424/185.1 |
| 2003/0018367 | A1 * | 1/2003 | DiLorenzo ...................... 607/46 |
| 2003/0031665 | A1 | 2/2003 | Dang et al. |
| 2003/0082201 | A1 | 5/2003 | Mukherjee et al. |
| 2003/0099663 | A1 | 5/2003 | Fleitmann et al. |
| 2004/0247570 | A1 * | 12/2004 | Miller et al. ................. 424/93.7 |
| 2005/0054594 | A1 | 3/2005 | Zhang et al. |
| 2005/0075701 | A1 | 4/2005 | Shafer |
| 2005/0075702 | A1 | 4/2005 | Shafer |
| 2005/0143787 | A1 | 6/2005 | Boveja et al. |
| 2005/0209625 | A1 | 9/2005 | Chan |
| 2006/0094924 | A1 | 5/2006 | Riehl |
| 2006/0149337 | A1 * | 7/2006 | John .............................. 607/45 |
| 2006/0167501 | A1 | 7/2006 | Ben-David et al. |
| 2006/0287678 | A1 * | 12/2006 | Shafer .............................. 607/2 |
| 2007/0191906 | A1 | 8/2007 | Iyer et al. |
| 2007/0255085 | A1 | 11/2007 | Kishawi et al. |
| 2008/0033398 | A1 | 2/2008 | Reed et al. |
| 2008/0114282 | A1 | 5/2008 | Carter |
| 2008/0228239 | A1 | 9/2008 | Tyler et al. |
| 2008/0306325 | A1 | 12/2008 | Burnett et al. |
| 2008/0306326 | A1 | 12/2008 | Epstein |
| 2008/0319506 | A1 | 12/2008 | Cauller |
| 2009/0149693 | A1 | 6/2009 | Dacey, Jr. et al. |
| 2009/0149694 | A1 | 6/2009 | Dacey, Jr. et al. |
| 2009/0149797 | A1 * | 6/2009 | Dacey et al. ..................... 604/20 |
| 2009/0149798 | A1 | 6/2009 | Dacey, Jr. et al. |
| 2009/0149799 | A1 | 6/2009 | Dacey, Jr. et al. |
| 2009/0149895 | A1 | 6/2009 | Dacey, Jr. et al. |
| 2009/0149896 | A1 | 6/2009 | Dacey, Jr. et al. |
| 2009/0149897 | A1 | 6/2009 | Dacey, Jr. et al. |
| 2009/0149911 | A1 | 6/2009 | Dacey, Jr. et al. |
| 2009/0149912 | A1 | 6/2009 | Dacey, Jr. et al. |
| 2009/0149914 | A1 | 6/2009 | Dacey, Jr. et al. |
| 2009/0149919 | A1 | 6/2009 | Dacey, Jr. et al. |
| 2009/0149926 | A1 | 6/2009 | Dacey, Jr. et al. |
| 2009/0157147 | A1 | 6/2009 | Cauller et al. |
| 2009/0175896 | A1 | 7/2009 | Bachmann et al. |
| 2009/0198450 | A1 | 8/2009 | Fernandez |
| 2009/0198451 | A1 | 8/2009 | Fernandez |

FOREIGN PATENT DOCUMENTS

| | | | |
|---|---|---|---|
| WO | WO 2005/094682 | A1 | 10/2005 |
| WO | WO 2008/046576 | A1 | 4/2008 |
| WO | WO 2008/088846 | A2 | 7/2008 |
| WO | WO 2009/003025 | A2 | 12/2008 |

OTHER PUBLICATIONS

Anderson et al.; "Effects of Iontophoresis Current Magnitude and Duration on Dexamethasone Deposition and Localized Drug Retention"; Physical Therapy; Feb. 2003; pp. 161-170; vol. 83, No. 2.

Ansel et al.; "Skin-Nervous System Interactions"; Progress in Dermatology; Jan. 1996; pp. 198-204; vol. 106, No. 1; Dermatology Foundation.

Beran et al.; "Intradermal influenza vaccination of healthy adults using a new microinjection system: a 3-year randomized controlled safety and immunogenicity trial"; BMC Medicine; Apr. 2, 2009; pp. 1-15; vol. 7, No. 13; BioMed Central Ltd.

Bernik et al.; "Pharmacological Stimulation of the Cholinergic Antiinflammatory Pathway"; J. Exp. Med.; Mar. 18, 2002; pp. 781-788; vol. 195, No. 6; The Rockefeller University Press.

Borovikova et al.; "Vagus nerve stimulation attenuates the systemic inflammatory response to endotoxin"; Nature; May 25, 2000; pp. 458-462; vol. 405; Macmillan Magazines Ltd.

Bour-Jordan et al.; "Sensory Neurons Link the Nervous System and Autoimmune Diabetes"; Cell; Dec. 15, 2006; pp. 1097-1099; Elsevier Inc.

Burssens et al.; Acta Orthop Belg.; Dec. 2003, (Abstract) pp. 528-532; vol. 69, No. 6.

Chernova et al.; "Substance P (SP) enhances CCL5-induced chemotaxis and intracellular signaling in human monocytes, which express the truncated neurokinin-1 receptor (NK1R)"; Journal of Leukocyte Biology; 2009; pp. 154-164; vol. 85; Society for Leukocyte Biology.

Dunzendorfer et al.; "Cutting Edge: Peripheral Neuropeptides Attract Immature and Arrest Mature Blood-Derived Dendritic Cells"; The Journal of Immunology; 2001; pp. 2167-2172; vol. 166; The American Association of Immunologists.

Elenkov et al.; "The Sympathetic Nerve—An Integrative Interface between Two Supersystems: The Brain and the Immune System"; Pharmacological Reviews; 2000; pp. 595-638; vol. 52, No. 4.

Gershon et al.; "A Phase I-II Study of Live Attenuated Varicella-Zoster Virus Vaccine to Boost Immunity in Human Immunodeficiency Virus-Infected Children with Previous Varicella"; The Pediatric Infectious Disease Journal; Jul. 2009; pp. 653-655; vol. 28, No. 7; Lippincott Williams & Wilkins.

Groneberg et al.; "Neurogenic mechanisms in bronchial inflammatory diseases"; Allergy; 2004; pp. 1139-1152; vol. 59; Blackwell Munksgaard.

Han, Ji-Sheng; "Acupuncture: neuropeptide release produced by electrical stimulation of different frequencies"; Trends in Neurosciences; Jan. 2003; pp. 17-22; vol. 26, No. 1.

Head et al.; "A Two-Year Study with Fibrillar β-Amyloid (Aβ) Immunization in Aged Canines: Effects on Cognitive Function and Brain Aβ"; The Journal of Neuroscience; Apr. 2, 2008; pp. 3555-3566; vol. 28, No. 14; Society for Neuroscience.

Helmuth, Laura; "Boosting Brain Activity From the Outside in"; Neuroscience; May 18, 2001; (Abstract) pp. 1284-1286; vol. 292, No. 5520.

Herzberg et al.; "Electrical stimulation of the sciatic nerve alters neuropeptide content and lymphocyte migration in the subcutaneous tissue of the rat hind paw"; NeuroReport; Sep. 11, 1995; pp. 1773-1777; vol. 6, No. 13; Rapid Science Publishers.

Holland et al.; "Intradermal Influenza Vaccine Administered Using a New Microinjection System Produces Superior Immunogenicity in Elderly Adults: A Randomized Controlled Trial"; The Journal of Infectious Diseases; Sep. 1, 2008; pp. 650-658; vol. 198; Infectious Diseases Society of America.

Johnston et al.; "Human T lymphocyte chemotaxis and adhesion induced by vasoactive intestinal peptide"; The Journal of Immunology; 1994; (Abstract) pp. 1762-1768; vol. 153, No. 4.

Kane et al.; "Protective effect of sensory denervation in inflammatory arthritis (evidence of regulatory neuroimmune pathways in the arthritic joint)"; Ann Rheum Dis; 2005; pp. 325-327; vol. 64.

Kaufman et al.; "Poxvirus-based vaccine therapy for patients with advanced pancreatic cancer"; Journal of Translational Medicine; Nov. 26, 2007; pp. 1-10; vol. 5, No. 60; BioMed Central Ltd.

Kaye et al.; "Transcutaneous Electrical Nerve Stimulation"; pp. 1-12; last accessed on May 13, 2009 at http://emedicine.medscape.com/article/325107-print.

Khalil et al.; "Effects of Aging on Neurogenic Vasodilator Responses Evoked by Transcutaneous Electrical Nerve Stimulation: Relevance to Wound Healing"; Journal of Gerontology: Biological Sciences; 2000; pp. B257-B263; vol. 55A, No. 6; The Gerontological Society of America.

Khalil et al.; "cis-Urocanic Acid Stimulates Neuropeptide Release from Peripheral Sensory Nerves"; J Invest Dermatol; 2001; pp. 886-891; vol. 117; The Society for Investigative Dermatology, Inc.

Kizaki et al.; "β2-Adrenergic receptor regulates Toll-like receptor-4-induced nuclear factor-κb activation through β-arrestin 2"; Immunology; 2008; pp. 348-356; vol. 124; Blackwell Publishing Company.

Koudelka et al.; "Interaction between a 54-Kilodalton Mammalian Cell Surface Protein and Cowpea Mosaic Virus"; Journal of Virology; Feb. 2007; pp. 1632-1640; vol. 81, No. 4; American Society for Microbiology.

Lam et al.; "Neurogenic component of different models of acute inflammation in the rat knee joint"; Annals of the Rheumatic Diseases; 1991; pp. 747-751; vol. 50.

Lambert et al.; "Neuropeptides and Langerhans cells"; Exp. Dermatol; 1998; pp. 73-80; vol. 7; Munksgaard.

Laurent et al.; "Evaluation of the clinical performance of a new intradermal vaccine administration technique and associated delivery system"; Vaccine; Dec. 17, 2007; (Abstract) pp. 8833-8842; vol. 25, No. 52.

Laurent et al.; "Echographic measurement of skin thickness in adults by high frequency ultrasound to assess the appropriate microneedle length for intradermal delivery of vaccines"; Vaccine; Aug. 21, 2007; (Abstract) pp. 6423-6430; vol. 25, No. 34.

Lele, P. P.; "Effects of Focused Ultrasonic Radiation on Peripheral Nerve, with Observations on Local Heating"; Experimental Neurology; 1963; pp. 47-83; vol. 8.

Levin et al.; "Administration of Live Varicella Vaccine to HIV-Infected Children with Current or Past Significant Depression of CD4+ T Cells"; The Journal of Infectious Diseases; Jul. 15, 2006; pp. 247-255; vol. 194; Infectious Diseases Society of America.

Levite, Mia; "Neurotransmitters activate T-cells and elicit crucial functions via neurotransmitter receptors"; Current Opinion in Pharmacology; 2008; pp. 460-471; vol. 8; Elsevier Ltd.

Levite et al.; "Neuropeptides, Via Specific Receptors, Regulate T Cell Adhesion to Fibronectin"; The Journal of Immunology; 1998; pp. 993-1000; vol. 160; The American Association of Immunologists.

Levite, Mia; "Neuropeptides, by direct interaction with T cells, induce cytokine secretion and break the commitment to a distinct T helper phenotype"; Proc. Natl. Acad. Sci. USA; Oct. 1998; pp. 12544-12549; vol. 95; The National Academy of Sciences.

Lewis, Jonathan J.; "Therapeutic cancer vaccines: Using unique antigens"; PNAS; Oct. 5, 2004; pp. 14653-14656; vol. 101, Suppl. 2; The National Academy of Sciences of the USA.

Manayani et al.; "A Viral Nanoparticle with Dual Function as an Anthrax Antitoxin and Vaccine"; PLoS Pathogens; Oct. 2007; pp. 1422-1431; vol. 3, No. 10.

Marchand et al.; "Role of the Immune System in Chronic Pain"; Nature Reviews; Jul. 2005; pp. 521-532; vol. 6; Nature Publishing Group.

McCormack et al.; "Ultra-short-course seasonal allergy vaccine (Pollinex Quattro)"; Drugs; 2006; (Abstract) pp. 931-938; vol. 66, No. 7.

McDougall, Jason J.; "Arthritis and pain: Neurogenic origin of joint pain"; Arthritis Research & Therapy; 2006; pp. 1-10; vol. 8, No. 220; BioMed Central Ltd.

Mignini et al.; "Autonomic innervation of immune organs and neuroimmune modulation"; Autonomic & Autocoid Pharmacology; pp. 1-25; vol. 23; Blackwell Publishing Ltd.

Nance et al.; "Autonomic Innervation and Regulation of the Immune System"; Brain Behav Immun.; Aug. 2007; pp. 736-745; vol. 21, No. 6.

Niizeki et al.; "A Substance p Agonist Acts as an Adjuvant to Promote Hapten-Specific Skin Immunity"; J Invest Dermatol; 1999; pp. 437-442; vol. 112; The Society for Investigative Dermatology, Inc.

Nilsson et al.; "Accumulation of CD8+ Cells After Immunization with Soluble Antigen"; Scand. J. Immunol.; 1990; pp. 53-57; vol. 31.

Norton, Stephen J.; "Can ultrasound be used to stimulate nerve tissue?"; Biomedical Engineering Online; Mar. 4, 2003; pp. 1-9; vol. 2, No. 6; BioMed Central Ltd.

Osherovich, Lev; "Cytos' cat and mouse game"; Science-Business eXchange; 2009; pp. 1-2; Nature Publishing Group.

Oxman et al.; "A Vaccine to Prevent Herpes Zoster and Postherpetic Neuralgia in Older Adults"; Jun. 2, 2005; pp. 2271-2284; vol. 352, No. 22; Massachusetts Medical Society.

Pavlov et al.; "Central muscarinic cholinergic regulation of the systemic inflammatory response during endotoxemia"; PNAS; Mar. 28, 2006; pp. 5219-5223; vol. 103, No. 13; The National Academy of Sciences of the USA.

Pavlov et al.; "The Cholinergic Anti-inflammatory Pathway: A Missing Link in Neuroimmunomodulation"; Molecular Medicine; May-Aug. 2003; pp. 125-134; vol. 9, Nos. 5-8.

Peckham et al.; "Functional Electrical Stimulation for Neuromuscular Applications"; Annu. Rev. Biomed. Eng.; 2005; pp. 327-360; vol. 7; Annual Reviews.

Peters et al.; "Neuropeptide Control Mechanisms in Cutaneous Biology: Physiological and Clinical Significance"; Journal of Investigative Dermatology; 2006; pp. 1937-1947; vol. 126; The Society for Investigative Dermatology.

Radulovic et al.; "Immunomodulatory Role of the Corticotropin-Releasing Factor"; Archivum Immunologiac et Therapiac Experimentalis; 2001; pp. 33-38; vol. 49.

Razavi et al.; "TRPV1+ Sensory Neurons Control β Cell Stress and Islet Inflammation in Autoimmune Diabetes"; Cell; Dec. 15, 2006; pp. 1123-1135; vol. 127; Elsevier Inc.

Riley et al.; "Vaccines in Development to Prevent and Treat Atherosclerotic Disease"; Cardiology in Review; Nov./Dec. 2008; pp. 288-300; vol. 16, No. 6; Lippincott Williams & Wilkins.

Roosterman et al.; "Neuronal Control of Skin Function: The Skin as a Neuroimmunoendocrine Organ"; Physiol Rev; 2006; pp. 1309-1379; vol. 86; American Physiological Society.

Saadéet al.; "Upregulation of proinflammatory cytokines and nerve growth factor by intraplantar injection of capsaicin in rats"; Journal of Physiology; 2002; pp. 241-253; vol. 545, No. 1; The Physiological Society.

Schlom et al.; "Cancer Vaccines: Moving Beyond Current Paradigms"; Clin Cancer Res; Jul. 1, 2007; pp. 3776-3782; vol. 13, No. 13; American Association for Cancer Research.

Scholzen et al.; "Effect of Ultraviolet Light on the Release of Neuropeptides and Neuroendocrine Hormones in the Skin: Mediators of Photodermatitis and Cutaneous Inflammation"; P. Journal of Investigative Dermatology Symposium Proceedings; 1999; pp. 55-60; vol. 4; The Society for Investigative Dermatology, Inc.

Scholzen et al.; "Neuropeptides in the skin: interactions between the neuroendocrine and the skin immune systems"; Exp Dermatol; Apr.-Jun. 1998; (Abstract) pp. 81-96; vol. 7, Nos. 2-3.

Schratzberger et al.; "Differential chemotactic activities of sensory neuropeptides for human peripheral blood mononuclear cells"; The Journal of Immunology; 1997;(Abstract) pp. 3895-3901; vol. 158, No. 8; The American Association of Immunologists.

Seidel et al.; "Substance P in Rheumatic Diseases"; Current Rheumatology Reviews; 2007; pp. 17-30; vol. 3; Bentham Science Publishers Ltd.

Seiffert et al.; "Neuroendocrine Regulation of Skin Dendritic Cells"; Ann. N.Y. Acad. Sci.; 2006; pp. 195-206; vol. 1088; New York Academy of Sciences.

Singer, Emily; "Tiny Implants for Treating Chronic Pain"; May 15, 2009; pp. 1-2; located at www.technologyreview.com/printer_friendly_article.aspx?id=2.

Steinhoff et al.; "Modern Aspects of Cutaneous Neurogenic Inflammation"; Arch Dermatol; Nov. 2003; pp. 1479-1488; vol. 139; American Medical Association.

Steinman, Lawrence; "Elaborate interactions between the immune and nervous systems"; Nature Immunology; Jun. 2004; vol. 5, No. 6.

Sternberg, Esther M.; "Neural regulation of innate immunity: a coordinated nonspecific host response to pathogens"; Nat Rev Immunol.; Apr. 2006; pp. 318-328; vol. 6, No. 4.

Theoharides et al.; "Critical role of mast cells in inflammatory diseases and the effect of acute stress"; Journal of Neuroimmunology; 2004; pp. 1-12; vol. 146; Elsevier B.V.

Tracey, Kevin J.; "The Inflammatory reflex"; Nature; Dec. 19/26, 2002; pp. 853-859; vol. 420; Nature Publishing Group.

Tsui et al.; "In vitro effects of ultrasound with different energies on the conduction properties of neural tissue"; Ultrasonics; 2005; pp. 560-565; vol. 43; Elsevier B.V.

Tyler et al.; "Remote Excitation of Neuronal Circuits Using Low-Intensity, Low-Frequency Ultrasound"; PLoS ONE; Oct. 2008; pp. 1-11; vol. 3, No. 10.

Veronesi et al.; "The TRPV1 Receptor: Target of Toxicants and Therapeutics"; Toxicological Sciences; 2006; pp. 1-3; vol. 89, No. 1; Oxford University Press on behalf of the Society of Toxicology.

Zhu et al.; "Toll like receptor-3 ligand poly-ICLC promotes the efficacy of peripheral vaccinations with tumor antigen-derived peptide epipodes in murine CNS tumor models"; Journal of Translational Medicine; 2007; pp. 1-15; Zhu et al.

MicroTransponder/Wireless Neurostimulation; pp. 1-5; located at http://www.microtransponder.com/about.html.

\* cited by examiner

DEVICE, METHOD, AND SYSTEM FOR NEURAL MODULATION AS VACCINE ADJUVANT IN A VERTEBRATE SUBJECT

CROSS-REFERENCE TO RELATED APPLICATIONS

The present application is related to and claims the benefit of the earliest available effective filing date(s) from the following listed application(s) (the "Related Applications") (e.g., claims earliest available priority dates for other than provisional patent applications or claims benefits under 35 USC §119(e) for provisional patent applications, for any and all parent, grandparent, great-grandparent, etc. applications of the Related Application(s)). All subject matter of the Related Applications and of any and all parent, grandparent, great-grandparent, etc. applications of the Related Applications is incorporated herein by reference to the extent such subject matter is not inconsistent herewith.

Related Applications:

For purposes of the USPTO extra-statutory requirements, the present application constitutes a continuation of U.S. patent application Ser. No. 12/655,195, entitled DEVICE, METHOD, AND SYSTEM FOR NEURAL MODULATION AS VACCINE ADJUVANT IN A VERTEBRATE SUBJECT, naming Gregory J. Della Rocca, Joshua L. Dowling, Eleanor V. Goodall, Roderick A. Hyde, Jordin T. Kare, Muriel Y. Ishikawa, Eric C. Leuthardt, Stephen L. Malaska, Nathan P. Myhrvold, Paul Santiago, Todd J. Stewart, Elizabeth A. Sweeney, Clarence T. Tegreene, Lowell L. Wood, Jr. and Victoria Y.H. Wood as inventors, filed 22 Dec. 2009, which is currently co-pending, or is an application of which a currently co-pending application is entitled to the benefit of the filing date.

The United States Patent Office (USPTO) has published a notice to the effect that the USPTO's computer programs require that patent applicants reference both a serial number and indicate whether an application is a continuation or continuation-in-part. Stephen G. Kunin, Benefit of Prior-Filed Application, USPTO Official Gazette Mar. 18, 2003, available at http://www.uspto.gov/web/offices/com/sol/og/2003/week11/patbene.htm. The present Applicant Entity (hereinafter "Applicant") has provided above a specific reference to the application(s)from which priority is being claimed as recited by statute. Applicant understands that the statute is unambiguous in its specific reference language and does not require either a serial number or any characterization, such as "continuation" or "continuation-in-part," for claiming priority to U.S. patent applications. Notwithstanding the foregoing, Applicant understands that the USPTO's computer programs have certain data entry requirements, and hence Applicant is designating the present application as a continuation-in-part of its parent applications as set forth above, but expressly points out that such designations are not to be construed in any way as any type of commentary and/or admission as to whether or not the present application contains any new matter in addition to the matter of its parent application(s).

SUMMARY

A method for enhancing an immune response to one or more immunogen in a vertebrate subject is described herein. The method includes providing at least one energy stimulus configured to modulate one or more nervous system components of the vertebrate subject, and administering one or more immunogen to the vertebrate subject, wherein the at least one energy stimulus and the one or more immunogen are provided in a combination and in a temporal sequence sufficient to enhance the immunogen-specific immune responses in the vertebrate subject. The method for enhancing an immune response to one or more immunogen in the vertebrate subject can include eliciting an immune response in the vertebrate subject. The method can further include eliciting, accelerating, prolonging, facilitating, or altering in form or type the immunogen-specific immune response when the at least one energy stimulus configured to modulate one or more nervous system components is provided in combination with administering specific vaccine immunogens to the vertebrate subject. A method for enhancing an immune response to one or more immunogen in a vertebrate subject to an infectious agent is described herein. A method for enhancing an immune response to one or more immunogen in a vertebrate subject in response to a neoplasm is described herein.

In an aspect, the at least one energy stimulus can include one or more of electrical energy, magnetic energy, electromagnetic energy, ultrasonic energy, acoustic energy, mechanical energy, or thermal energy. The at least one energy stimulus can include at least one energy characteristic having one or more of waveform, frequency, amplitude, or duration. The one or more immunogen can include one or more of a bacterial antigen, a viral antigen, a fungal antigen, or a parasital antigen. The one or more immunogen can include a tumor antigen. The one or more immunogen can include one or more of a polypeptide, a lipid, a carbohydrate, a lipopolysaccharide, a nucleic acid, a peptide mimetic, a viral antigen, a bacterial antigen, a carcinoembryonic antigen, a mucin, a glycosphingolipid, a genetically engineered antigen, an antigen designed in silico, or a synthetic antigen. The at least one energy stimulus and immunogen can be provided simultaneously. The at least one energy stimulus can be provided prior to administering the immunogen. The immunogen can be provided prior to providing the at least one energy stimulus. The at least one energy stimulus and the immunogen can be provided at one administration site. The at least one energy stimulus and the immunogen can be provided at different administration sites. The at least one energy stimulus and the immunogen can be provided as a booster immunization.

The method can further include providing one or more transducer configured to direct the at least one energy stimulus to a tissue. The method can further include providing an energy generator to provide the at least one energy stimulus. The energy generator can include one or more transducer configured to direct the at least one energy stimulus to a tissue. The method can further include providing the at least one energy stimulus to a tissue near an immunogen administration site. In the method, modulating the one or more nervous system components can include stimulating the one or more nervous system components in the vertebrate subject. In the method, modulating can further include the one or more nervous system components including inhibiting the one or more nervous system components in the vertebrate subject.

The method for modulating the one or more nervous system components can include modulating release of a neurotransmitter. In an aspect, the neurotransmitter can modulate one or more nerve impulses in the vertebrate subject. In the method, modulating release can include stimulating release of the neurotransmitter. In the method, modulating release can include inhibiting release of the neurotransmitter. The neurotransmitter can modulate a function of one or more cells of the vertebrate subject. The one or more cells can include nerve cells. The one or more cells can include the same cells that released the neurotransmitter. The one or more cells can include a non-nervous system cell type. The neurotransmitter can include a glucocorticoid, norepinephrine, noradrenalin, neuropeptide Y, substance P, CGRP, NGF or VIP.

In an aspect, the at least one energy stimulus can be provided to the vertebrate subject within a region of an immunogen administration site. The at least one energy stimulus can be provided to a tissue of the vertebrate subject in the vicinity of a lymph node, wherein the lymph node is located within a region of an immunogen administration site of the vertebrate subject. The at least one energy stimulus can be configured to elicit a systemic neurogenic response in the vertebrate subject. The at least one energy stimulus can be configured to elicit a local neurogenic response in the vertebrate subject. The at least one energy stimulus can be provided to a tissue of the vertebrate subject and configured to enhance a response involving a lymphoid organ, thymus, spleen, bone marrow, peritoneum, mucosal tissue, or a portion of a digestive tract. In an aspect, an application pattern of the at least one energy stimulus can include one or more of a cyclical pattern, intermittent pattern, repetitive pattern, random pattern, or non-random pattern. In an aspect of the method, providing the application pattern can include applying the pattern at one or more sites.

In an aspect, the method for enhancing the immune response in the vertebrate subject can include enhancing an immune response against an infectious disease, a prion disease, a neoplastic disease, a heart disease, a respiratory disease, an autoimmune disease, a hyperimmune disease, or an allergic response. In an aspect, the method for enhancing the immune response in the vertebrate subject can include enhancing an immune response to prevent an infectious disease, a prion disease, a neoplastic disease, a heart disease, a respiratory disease, an autoimmune disease, a hyperimmune disease, or an allergic response. The vertebrate subject can include a mammal, an avian, a reptile, an amphibian, an osteichthye, or a chondrichthyes. In an aspect, the method for providing the one or more immunogen can include administering the one or more immunogen to the vertebrate subject by parenteral route, subcutaneous route, intradermal route, intravenous route, intramuscular route, intraperitoneal route, transdermal route, transcutaneous route, transbuccal route, intraocular route, intravaginal route, oral route, intrarectal route, inhalation route, intra-nasal route, depot injection, or tissue implantation. In an aspect, the method for providing the one or more immunogen can include delivering the one or more immunogen to the vertebrate subject using one or more of a microneedle, a microfine lance, a microfine cannula, a microinjector, a jet fluid injector, a high pressure jet fluid injector, or a tissue implant. In an aspect, the method for providing the one or more immunogen can include delivering the one or more immunogen to the vertebrate subject using one or more of iontophoresis, microdialysis, ultrafiltration, electromagnetics, osmosis, electroosmosis, sonophoresis, electroporation, thermal poration, microporation, skin permeabilization, or laser. In an aspect, the method can further include providing one or more compounds to the vertebrate subject including an adjuvant, a hapten, an immunomodulatory compound, a cytokine, a chemokine, a growth factor, or a cell-signaling compound.

A method for enhancing an immune response to an infectious agent in a vertebrate subject is described herein. The method includes providing at least one energy stimulus configured to modulate one or more nervous system components of the vertebrate subject, and administering one or more immunogen to the vertebrate subject, wherein the at least one energy stimulus and the one or more immunogen are provided in a combination and in a temporal sequence sufficient to enhance the immunogen-specific immune responses in the vertebrate subject.

A method for enhancing an immune response to a neoplasm in a vertebrate subject is described herein. The method includes providing at least one energy stimulus configured to modulate one or more nervous system components of the vertebrate subject, and administering one or more immunogen to the vertebrate subject, wherein the at least one energy stimulus and the one or more immunogen are provided in a combination and in a temporal sequence sufficient to enhance the immunogen-specific immune responses in the vertebrate subject.

A system is described herein that includes an apparatus comprising an energy generator to provide at least one energy stimulus configured to modulate one or more nervous system components of the vertebrate subject, and a device configured to administer one or more immunogen to the vertebrate subject. In further aspects, the system can provide the at least one energy stimulus and can administer the one or more immunogen in a combination and in a temporal sequence sufficient to elicit, accelerate, prolong, facilitate or alter in form or type, or enhance immunogen-specific immune responses when used in combination with specific vaccine immunogens in the vertebrate subject. The apparatus can be configured to provide the at least one energy stimulus and the device can be configured to provide the one or more immunogen in a combination and in a temporal sequence sufficient to enhance an immune response in the vertebrate subject. In an aspect, the at least one energy stimulus can include one or more of electrical energy, magnetic energy, electromagnetic energy, ultrasonic energy, acoustic energy, mechanical energy, or thermal energy. The at least one energy stimulus can include at least one energy characteristic having one or more of waveform, frequency, amplitude, or duration.

The system including the at least one energy stimulus can include an electrical stimulus in combination with an ultrasonic stimulus. The at least one energy stimulus can include an electrical stimulus in combination with a magnetic stimulus. The at least one energy stimulus can include an electrical stimulus in combination with a mechanical stimulus. The system further includes the device including one or more reservoirs including at least one of the one or more immunogens or one or more adjuvants. The system can further include circuitry configured in a temporal sequence to provide the at least one energy stimulus configured to modulate the one or more nervous system components in the vertebrate subject, and to provide one or more immunogen to the vertebrate subject. The one or more immunogen can include one or more of a bacterial antigen, a viral antigen, a fungal antigen, or a parasital antigen. The one or more immunogen can include a tumor antigen. The one or more immunogen can include one or more of a polypeptide, a lipid, a carbohydrate, a lipopolysaccharide, a nucleic acid, a peptide mimetic, a viral antigen, a bacterial antigen, a carcinoembryonic antigen, a mucin, a glycosphingolipid, a genetically engineered antigen, an antigen designed in silico, or a synthetic antigen. The system can further include circuitry for one or more transducer configured to direct the at least one energy stimulus to a tissue. The system including circuitry for the apparatus configured to provide the at least one energy stimulus and circuitry for the device configured to deliver the immunogen can be configured to act simultaneously.

The system including the apparatus and the device can be enclosed in a single unit. The apparatus and the device can be enclosed in two or more units, wherein the two or more units are configured to be substantially in communication. The at least one energy stimulus can include an excitatory stimulus directed to the one or more nervous system components. The at least one energy stimulus can include an inhibitory stimulus directed to the one or more nervous system components. The at least one energy stimulus can be configured to modulate release of a neurotransmitter. The neurotransmitter can be configured to provoke an excitatory nerve impulse in the vertebrate subject. The neurotransmitter can be configured to provoke an inhibitory nerve impulse in the vertebrate subject. The neurotransmitter can include, but is not limited to, a glucocorticoid, norepinephrine, noradrenalin, neuropeptide Y, substance P, CGRP, NGF or VIP. The apparatus can be configured to provide the at least one energy stimulus to the vertebrate subject within a region of an immunogen administration site of the vertebrate subject. The apparatus can be configured to provide the at least one energy stimulus to the vertebrate subject in a location configured to stimulate a lymph node within the region of the immunogen administration site. The at least one energy stimulus can be configured to stimulate one or more of a lymphoid organ, thymus, spleen, bone marrow, peritoneum, mucosal tissue, or a portion of a digestive tract of the vertebrate subject. The at least one energy stimulus can be configured to elicit a systemic neurogenic response in the vertebrate subject. The at least one energy stimulus is can be to elicit a local neurogenic response in the vertebrate subject. The apparatus can be configured to provide the at least one energy stimulus in an application pattern that includes at least one energy characteristic having one or more of waveform, frequency, amplitude, or duration, to elicit the neurogenic response in the vertebrate subject. The application pattern of the at least one energy stimulus can include, but is not limited to, a cyclical pattern, an intermittent pattern, a repetitive pattern, a random pattern, or a non-random pattern.

The system including the device configured to deliver the one or more immunogens can include one or more of a microneedle, a microfine lance, a microfine cannula, a microinjector, a jet fluid injector, a high pressure jet fluid injector, or a tissue implant. The device configured to deliver the one or more immunogens can include one or more of transdermal delivery devices transcutaneous delivery devices, percutaneous delivery devices, intradermal delivery devices, or implantable delivery devices. At least a portion of the apparatus configured to deliver the at least one energy stimulus can be implantable. The apparatus configured to deliver the at least one energy stimulus can be configured to deliver the at least one energy stimulus to the one or more nervous system components of the vertebrate subject from a site external to the vertebrate subject. The vertebrate subject can include, but is not limited to, a mammal, an avian, a reptile, an amphibian, an osteichthye, or a chondrichthyes. The one or more immunogen can be configured for administration to the vertebrate subject by one or more of parenteral route, subcutaneous route, intradermal route, intravenous route, intramuscular route, intraperitoneal route, transdermal route, transcutaneous route, transbuccal route, intraocular route, intravaginal route, oral route, intrarectal route, inhalation route, intranasal route, depot injection, or tissue implantation.

A device is described herein that includes an energy generator providing at least one energy stimulus to modulate one or more nervous system components of a vertebrate subject and an apparatus configured to deliver one or more immunogen to the vertebrate subject. In an aspect, the energy generator can provide the at least one energy stimulus and the apparatus can be configured to administer the one or more immunogen in a combination and in a temporal sequence sufficient to enhance an immunogen-specific immune response in the vertebrate subject.

In an aspect, the at least one energy stimulus can include one or more of electrical energy, magnetic energy, electromagnetic energy, ultrasonic energy, acoustic energy, mechanical energy, or thermal energy. The at least one energy stimulus can include at least one energy characteristic having one or more of waveform, frequency, amplitude, or duration. The system including the at least one energy stimulus can include an electrical stimulus in combination with an ultrasonic stimulus. The at least one energy stimulus can include an electrical stimulus in combination with a magnetic stimulus. The at least one energy stimulus can include an electrical stimulus in combination with a mechanical stimulus. The device further includes the device including one or more reservoirs including at least one of the one or more immunogens or one or more adjuvants. The device can further include circuitry configured in a temporal sequence to provide the at least one energy stimulus configured to modulate the one or more nervous system components in the vertebrate subject, and to provide one or more immunogen to the vertebrate subject. The one or more immunogen can include one or more of a bacterial antigen, a viral antigen, a fungal antigen, or a parasital antigen. The one or more immunogen can include a tumor antigen. The one or more immunogen can include one or more of a polypeptide, a lipid, a carbohydrate, a lipopolysaccharide, a nucleic acid, a peptide mimetic, a viral antigen, a bacterial antigen, a carcinoembryonic antigen, a mucin, a glycosphingolipid, a genetically engineered antigen, an antigen designed in silico, or a synthetic antigen.

The device can include energy generator providing the at least one energy stimulus and the apparatus can be configured to deliver the one or more immunogen is provided simultaneously. The energy generator providing the at least one energy stimulus can be provided prior to providing the apparatus configured to deliver the one or more immunogen. The apparatus configured to deliver the one or more immunogen can be provided prior to providing the energy generator providing the at least one energy stimulus. The energy generator providing the at least one energy stimulus and the apparatus configured to deliver the one or more immunogen can be provided at one administration site. The energy generator providing the at least one energy stimulus and the apparatus configured to deliver the one or more immunogen can be provided at different administration sites. The energy generator providing the at least one energy stimulus and the apparatus configured to deliver the one or more immunogen can be provided as a booster immunization. The energy generator and the apparatus can be enclosed in a single unit. The energy generator and the apparatus can be enclosed in two or more units, wherein the two or more units can be configured to be substantially in communication. The energy generator can include one or more transducer configured to direct the at least one energy stimulus. The at least one energy stimulus can include an excitatory stimulus directed to the one or more nervous system components. The at least one energy stimulus can include an inhibitory stimulus directed to the one or more nervous system components. The at least one energy stimulus can be configured to modulate release of a neurotransmitter. The neurotransmitter can be configured to provoke an excitatory nerve impulse in the vertebrate subject. The neurotransmitter can be configured to provoke an inhibitory nerve impulse in the vertebrate subject. The neurotransmitter can include, but is not limited to, a glucocorticoid, norepinephrine, noradrenalin, neuropeptide Y, substance P, CGRP, NGF or VIP. The at least one energy stimulus can be provided to the vertebrate subject within a region of an immunogen administration site in the vertebrate subject. The at least one energy stimulus can be provided to the vertebrate subject in a location configured to stimulate a lymph node within the region of the immunogen administration site. The at least one energy stimulus can be configured to stimulate one or more of a lymphoid organ, thymus, spleen, bone marrow, peritoneum, mucosal tissue, or a portion of a digestive tract of the vertebrate subject. The at least one energy stimulus can be configured to elicit a systemic neurogenic response in the vertebrate subject. The at least one energy stimulus can be configured to elicit a local neurogenic response in the vertebrate subject. The at least one energy stimulus can be provided in an application pattern including at least one energy characteristic having one or more of waveform, frequency, amplitude, or duration, to elicit the neurogenic response in the vertebrate subject. The application pattern can include one or more of a cyclical pattern, an intermittent pattern, a repetitive pattern, a random pattern, or a non-random pattern. The vertebrate subject can include, but is not limited to, a mammal, an avian, a reptile, an amphibian, an osteichthye, or a chondrichthyes. The one or more immunogen can be configured for administration to the vertebrate subject by one or more of parenteral route, subcutaneous route, intradermal route, intravenous route, intramuscular route, intraperitoneal route, transdermal route, transcutaneous route, transbuccal route, intraocular route, intravaginal route, oral route, intrarectal route, inhalation route, intra-nasal route, depot injection, or tissue implant. The apparatus configured to deliver the one or more immunogens can include one or more of microneedles, microfine lances, microfine cannulas, microinjector, jet fluid injector, high pressure jet fluid injector, or tissue implant. The apparatus configured to deliver the one or more immunogens can include one or more of transdermal delivery devices, transcutaneous delivery devices, percutaneous delivery devices, intradermal delivery devices, or implantable delivery devices. At least a portion of the energy generator configured to deliver the at least one energy stimulus can be implantable. The energy generator configured to deliver the at least one energy stimulus can be configured to deliver the at least one energy stimulus to the one or more nervous system components of the vertebrate subject from a site external to the vertebrate subject.

A method for vaccinating a vertebrate subject against a disease is described herein that includes providing at least one energy stimulus configured to modulate one or more nervous system components of the vertebrate subject, and administering one or more immunogen to the vertebrate subject, wherein the at least one energy stimulus and the one or more immunogen are provided in a combination and in a temporal sequence sufficient to accelerate, prolong, facilitate, or alter in form or type the immune response in the vertebrate subject. The at least one energy stimulus can include one or more of electrical energy, magnetic energy, electromagnetic energy, ultrasonic energy, acoustic energy, mechanical energy, or thermal energy. The at least one energy stimulus can include at least one energy characteristic having one or more of waveform, frequency, amplitude, or duration. The one or more immunogen can include one or more of a bacterial antigen, a viral antigen, a fungal antigen, or a parasital antigen. The one or more immunogen can include a tumor antigen. In the method, enhancing the immune response in the vertebrate subject can be configured to treat an infectious disease, a prion disease, a neoplastic disease, a heart disease, a respiratory disease, an autoimmune disease, a hyperimmune disease, or an allergic response. In an aspect, the method for enhancing the immune response in the vertebrate subject can be configured to prevent an infectious disease, a prion disease, a neoplastic disease, a heart disease, a respiratory disease, an autoimmune disease, a hyperimmune disease, or an allergic response. The one or more immunogens can be self-administered prior to providing the at least one energy stimulus. The one or more immunogens can be self-administered after providing the at least one energy stimulus.

A system for enhancing an immune response in a vertebrate subject is described herein that includes circuitry for an energy generator providing at least one energy stimulus configured to modulate one or more nervous system components of a vertebrate subject, and circuitry for an apparatus configured to deliver one or more immunogen to the vertebrate subject. The system can further include the circuitry for the energy generator providing the at least one energy stimulus and the circuitry for the vaccine delivery apparatus providing the one or more immunogen in a combination and in a temporal sequence sufficient to enhance an immune response in the vertebrate subject. The at least one energy stimulus can include one or more of an electrical stimulus, a magnetic stimulus, an electromagnetic stimulus, an ultrasonic stimulus, an acoustic stimulus, a mechanical stimulus, or a thermal stimulus. The at least one energy stimulus can include at least one energy characteristic having one or more of waveform, frequency, amplitude, or duration.

The foregoing summary is illustrative only and is not intended to be in any way limiting. In addition to the illustrative aspects, embodiments, and features described above, further aspects, embodiments, and features will become apparent by reference to the drawings and the following detailed description.

DETAILED DESCRIPTION

Figure 1:
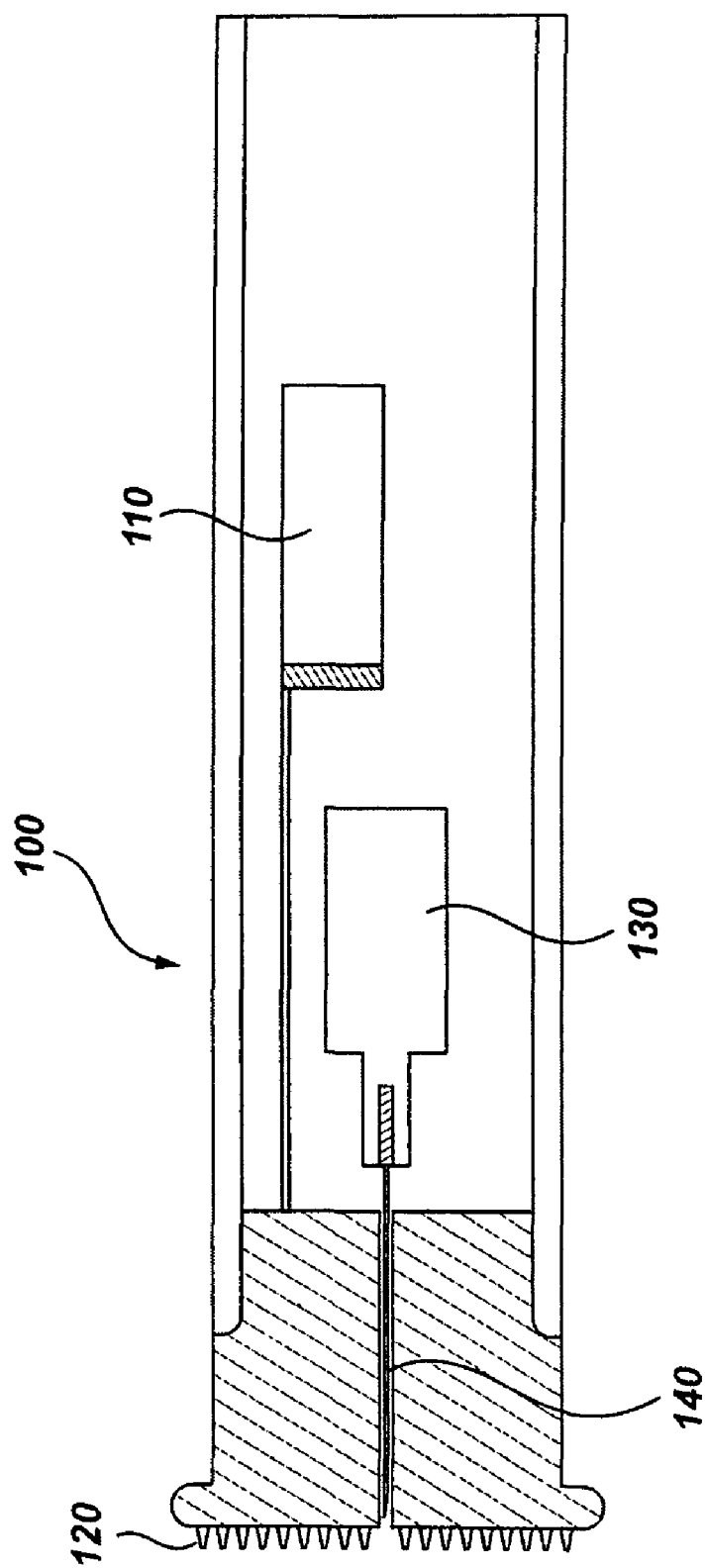
FIG. 1 depicts a diagrammatic view of one aspect of an embodiment of a device configured to modulate an immune response in a vertebrate subject.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

The present application uses formal outline headings for clarity of presentation. However, it is to be understood that the outline headings are for presentation purposes, and that different types of subject matter may be discussed throughout the application (e.g., method(s) may be described under composition heading(s) and/or kit headings; and/or descriptions of single topics may span two or more topic headings). Hence, the use of the formal outline headings is not intended to be in any way limiting.

A method for enhancing an immune response to one or more immunogen in a vertebrate subject is described herein. The method includes providing at least one energy stimulus configured to modulate one or more nervous system components of the vertebrate subject, and administering one or more immunogen to the vertebrate subject, wherein the at least one energy stimulus and the one or more immunogen are provided in a combination and in a temporal sequence sufficient to enhance the immunogen-specific immune response in the vertebrate subject. The method for enhancing an immune response to one or more immunogen in the vertebrate subject can include eliciting an immune response in the vertebrate subject. The method for enhancing an immune response can include eliciting, accelerating, prolonging, facilitating, or altering in form or type the immunogen-specific immune response in the vertebrate subject. The method includes the at least one energy stimulus configured to modulate one or more nervous system components provided in combination with administering specific vaccine immunogens to the vertebrate subject. The method including the at least one energy stimulus can further have an adjuvant effect on the immunogen-specific immune response and thereby reducing the amount of immunogen required to be administered to achieve an adequate immune response to treat a disease or condition in the vertebrate subject. A method for enhancing an immune response to one or more immunogen in a vertebrate subject including enhancing an immune response to a pathology-related agent is described herein. A method for enhancing an immune response to one or more immunogen in a vertebrate subject including enhancing an immune response to an infectious agent is described herein. A method for enhancing an immune response to one or more immunogen in a vertebrate subject including enhancing an immune response to a neoplasm is described herein.

A method for enhancing an immune response to one or more immunogen in a vertebrate subject is described herein. The method includes providing at least one energy stimulus configured to modulate one or more nervous system component of the vertebrate subject. The at least one energy stimulus is provided to the vertebrate subject in combination with administering one or more immunogen, e.g., a bacterial antigen, a viral antigen, a fungal antigen, a parasital antigen, or a tumor antigen. The at least one energy stimulus and the one or more immunogen can be provided in one or more combinations and in one or more temporal sequences sufficient to enhance the immune response in the vertebrate subject. The method can be provided for enhancing an immune response in the vertebrate subject to, an infectious agent or for enhancing an immune response in the vertebrate subject to a neoplasm. The one or more immunogen can further include, but is not limited to, one or more of a polypeptide, lipid, carbohydrate, lipopolysaccharide, peptide mimetic, a viral antigen, a bacterial antigen, a carcinoembryonic antigen, a mucin, a glycosphingolipid, a genetically engineered antigen, an antigen designed in silico, or synthetic antigen.

In an aspect, the at least one energy stimulus can be provided to a tissue of the vertebrate subject and configured to enhance a response involving a lymphoid organ, thymus, spleen, bone marrow, peritoneum, mucosal tissue, or a portion of a digestive tract. The tissue of the digestive tract can be, for example, gastric-associated lymphoid tissue (GALT). In detailed aspects, the method can provide the at least one energy stimulus and can administer the one or more immunogen, and can be implemented in various combinations and in various temporal sequences to enhance the immune response in the vertebrate subject, e.g., wherein the at least one energy stimulus and immunogen are provided simultaneously; wherein the at least one energy stimulus is provided prior to administering the immunogen; wherein the immunogen is administered prior to providing the energy stimulus; wherein the at least one energy stimulus and the immunogen are provided at one administration site; wherein the at least one energy stimulus and the immunogen are provided at different administration sites; or wherein the at least one energy stimulus and the immunogen are provided as a booster immunization. The method that includes providing the at least one energy stimulus configured to modulate one or more nervous system components and administering the one or more immunogen to the vertebrate subject can occur over a range of time periods from approximately one or more seconds, approximately one or more minutes, approximately one or more hours or approximately one or more days.

The method can include providing one or more transducer configured to direct the at least one energy stimulus to a tissue. The method can further include providing an energy generator to provide the energy stimulus. In detailed aspects, the energy generator can include one or more transducer configured to direct the energy stimulus to one or more nervous system components in a region of an immunogen administration site. The one or more transducer configured to direct the energy stimulus to the one or more nervous system components can include one or more of an electrical stimulus, a magnetic stimulus, electromagnetic stimulus, ultrasonic stimulus, acoustic stimulus, mechanical stimulus, or thermal stimulus. The energy stimulus can also be provided in a combination, for example, wherein the energy stimulus includes an electrical stimulus in combination with an ultrasonic stimulus; wherein the energy stimulus includes an electrical stimulus in combination with a magnetic stimulus; or wherein the energy stimulus includes an electrical stimulus in combination with a mechanical stimulus. The energy stimulus can include one or more energy characteristic, e.g., one or more of a waveform, frequency, amplitude, or duration. The energy stimulus can also be provided in a sequential regimen. For example, and without limitation, the energy stimulus is an electrical stimulus that may be followed by an ultrasonic stimulus; or wherein the energy stimulus is an ultrasonic stimulus followed by a magnetic stimulus; or wherein the energy stimulus is an electrical stimulus followed by a mechanical stimulus.

In some aspects, the energy stimulus can include stimulating the nervous system component in the vertebrate subject. In further aspects, the energy stimulus can include inhibiting the nervous system component in the vertebrate subject. In further aspects, the energy stimulus can provide an excitatory stimulus or an inhibitory stimulus directed to the nervous system component. In detailed aspects, the energy stimulus can include inhibiting a nervous system component, e.g. a component that is a negative regulator of the immune response in the vertebrate subject. The excitatory stimulus or the inhibitory stimulus can be directed with regards to affecting an action potential in the nervous system component. The energy stimulus can influence the interaction between the nervous system and the immune system, which can occur locally, as through neurogenic inflammation and immunocyte activation, regionally, as through cell migration and effects within immune organs and tissues, and/or centrally, for example, by controlling inflammatory pathways or cytokine secretion. See, e.g., Peters, et al., *J. Invest. Derm.* 126: 1937-1947, 2006; Roosterman, et al., *Physiol Rev* 86: 1309-1379, 2006 Neuronal Control of Skin Function: The Skin as a Neuroimmunoendocrine Organ; Herzberg et al., *Neuroreport*, 6: 1773-1777, 1995; Nance, et al., Autonomic Innervation and Regulation of the Immune System (1987-2007) *Brain Behav Immun.* 21(6): 736-745, 2007; each of which is incorporated herein by reference. In some aspects, the energy stimulus can modulate release of a neurotransmitter from the nervous system component. In detailed aspects, the energy stimulus can inhibit, block, or negate release of a neurotransmitter or other nervous system component. In further detailed aspects, the energy stimulus can stimulate, enhance, or promote release of a neurotransmitter or other nervous system component. In detailed aspects, the energy stimulus is configured to modify, elicit, excite, stimulate, enhance, promote, mediate, induce, prolong, augment, facilitate, or alter in form or type the immunogen-specific immune response in the vertebrate subject. The method can further include providing one or more transducer configured to direct the energy stimulus to a tissue. The one or more transducer can convert a non-electrical parameter (e.g., sound, pressure or light) into electrical signals or vice versa. A transducer can be provided in any device, such as a piezoelectric crystal, microphone, or photoelectric cell that converts input energy of one form into output energy of another. Stimulator or actuator refers to components of a device that impart a stimulus (e.g., vibrotactile, electrotactile, or thermal) to tissue of a subject. A stimulator provides an example of a transducer. Unless described to the contrary, embodiments described herein that utilize stimulators or actuators may also employ other forms of transducers. See, e.g., U.S. Patent Applications 2008/0228239; U.S. 2009/0198451; U.S. 2009/0198450, each of which is incorporated herein by reference.

In some aspects of the method, the energy stimulus can modulate release of one or more neurotransmitters from the nervous system component. For example, the energy stimulus can stimulate release of the neurotransmitter or can inhibit release of the neurotransmitter from the nervous system component. Neurotransmitters, including neuropeptides, are important for various aspects of function and communication in the nervous system, as well as for directing interaction between the nervous system and immune system. Neurotransmitters can include, for example, glucocorticoids, norepinephrine, noradrenalin, neuropeptide Y, substance P, calcitonin gene-related peptide (CGRP), nerve growth factor (NGF) or vasoactive intestinal peptide/pituitary adenylate cyclase-activating polypeptide (VIP/PACAP), Modulating the release of a neurotransmitter can include inducing, increasing, inhibiting, blocking, or decreasing the release of the neurotransmitter and can include increased or decreased production of the neurotransmitter or its genetic precursor, such as RNA. Modulation of release of a neurotransmitter can include increasing, inducing, enhancing, promoting, stimulating, eliciting, exciting, augmenting, altering, mediating, or inducing release of a neurotransmitter. Modulation of release of a neurotransmitter can include inhibiting, decreasing, blocking, or negating release of the transmitter. A neurotransmitter, e.g., when released, increased, decreased, or inhibited, can affect, e.g., inhibit, block, or negate, release of a neurotransmitter to regulate an immune response in the vertebrate subject. A neurotransmitter, e.g., when released, increased, decreased, or inhibited, can affect, e.g., elicit, induce, increase, inhibit, lessen, block, or negate an immune response in the vertebrate subject. Neuropeptides can affect immune responses, for example vasodilation, mediator release, antigen presentation or T-cell activation. In addition to innervation of the skin, primary and secondary lymphoid organs are densely innervated. Antigen presenting cells (APC) and T-cells infiltrating the skin are subject to stimulatory and inhibitory neuropeptide signaling in the skin as well as in lymphoid tissues. See, e.g., Peters, et al., *J. Invest. Derm.* 126: 1937-1947, 2006; Dunzendorfer et al., The *J Immun*, 166:2167-2172, 2001; Peripheral Neuropeptides Attract Immature and Arrest Mature Blood-Derived Dendritic Cells; and Steinhoff, et al., *Arch Dermatol.* 139:1479-1488, 2003; Modern Aspects of Cutaneous Neurogenic Inflammation; each of which is incorporated herein by reference.

For example, a glucocorticoid is a neurotransmitter in vertebrate nerve cells that when inhibited results in an increased immune response in a vertebrate subject. Inhibition of the glucocorticoid biosynthesis or glucocorticoid activity in nerve cells of a vertebrate subject in combination with administration of an immunogen to the vertebrate subject can increase a $CD4^+$ T cell-mediated immune response to the immunogen in the vertebrate subject. See, e.g., WO 2008/046576, which is incorporated herein by reference.

In further aspects, an intraluminal electrode apparatus can provide an inhibitory signal to vagus nerve in a human subject inhibiting release of a neurotransmitter, e.g., acetylcholine. Inhibition of acetylcholine release from the vagus nerve in the human subject can be useful for enhancing an immune response in the human subject. The inhibitory signal is provided by an intraluminal electrode apparatus applied via the esophagus of a human subject in need of disease treatment. Such an apparatus is configured to provide an electrical signal of a type selected to generate a blocking signal to a vagal nerve situated external to the alimentary tract. See, e.g. U.S. Pat. No. 7,444,183 "Intraluminal electrode apparatus and method", which is incorporated herein by reference. Acetylcholine, the principal vagus nerve neurotransmitter, inhibits cytokine release from resident tissue macrophages, a process termed the "cholinergic antiinflammatory pathway". Vagotomy can decrease or eliminate an anti-inflammatory response; functionally, a vagal nerve block is a reversible vagotomy. A transient decrease or absence in an anti-inflammatory response can allow for an enhanced immune response, e.g., increased or prolonged immune response, to an immunogen in a vertebrate subject.

The method described herein includes providing at least one energy stimulus configured to modulate one or more nervous system components and administering one or more immunogen to enhance an immune response to the one or more immunogen in the vertebrate subject, wherein the immune response may be a specific type of immune response, for example, a humoral or cell-mediated immune response, an IgA-mediated immune response, an IgG-mediated immune response, an IgM-mediated immune response, a primary to secondary immune response switch, or a T cell-mediated immune response.

Neurotransmitters, including neuropeptides, can bind to receptors expressed not only on various "classical" target cells within the central or peripheral nervous system, but also on lymphocytes and other cell types. Binding can potently activate vital human T-cell functions needed for the T-cells to perform their specialized tasks, such as cytokine secretion, adhesion to extracellular matrix (ECM), migration, trafficking in and out of specific organs, and eradication of infectious organisms or cancer cells, In fact, both activating and suppressing effects of neurotransmitters on T-cells have been reported, depending on the neurotransmitter. Examples of activating neurotransmitters include "small" neurotransmitters such dopamine, glutamate and serotonin, and neuropeptides such as substance P, VIP, GnRH-I, GnRH-II, and somatostatin. See e.g., Levite, *Current Opinion in Pharmacology*, 8: 460-471, 2008; "Neurotransmitters activate T-cells and elicit crucial functions via neurotransmitter receptors"; Saadé

NE et al., *J Physiol.* 545: 241-253, 2002; "Upregulation of proinflammatory cytokines and nerve growth factor by intraplantar injection of capsaicin in rats"; and Herzberg et al., *Neuroreport,* 6: 1773-1777, 1995; "Electrical stimulation of the sciatic nerve alters neuropeptide content and lymphocyte migration in the subcutaneous tissue of the rat hind paw"; each of which is incorporated herein by reference.

In further aspects, a method for enhancing an immune response to one or more immunogen in a vertebrate subject includes providing an energy stimulus configured to modulate one or more nervous system components of the vertebrate subject, wherein the energy stimulus is provided in combination with administering one or more immunogen to the vertebrate subject. Stimulating the nervous system component can include stimulating components of the central nervous system (CNS) and/or the peripheral nervous system (PNS). The central nervous system (CNS) includes the brain, spinal cord, optic nerves and retina. The peripheral nervous system (PNS) includes nerves in the body that lie outside of the brain and spinal cord, e.g., the cranial nerves, spinal nerves, nerve plexuses, and their associated spinal and autonomic ganglia. The autonomic nervous system (ANS) includes a portion of the nervous system that regulates involuntary body functions, including, but not limited to, heart and circulation, respiration, digestion, and temperature regulation. The autonomic nervous system includes two divisions, the sympathetic nervous system and the parasympathetic nervous system. The sympathetic nervous system includes a division of the autonomic nervous system, that, broadly speaking, functions to mobilize the body's energy and resources during times of stress and arousal to prepare for "fight or flight", e.g., one or more of accelerated heart rate, constricted blood vessels, elevated blood pressure. The parasympathetic nervous system includes a division of the autonomic nervous system that regulates body functions during relaxed states.

In some aspects, the method includes providing an energy stimulus to one or more nervous system components in combination with administering one or more immunogen to the vertebrate subject, wherein the method can further include stimulating one or more peripheral cutaneous nerves that innervate one or more limbs of the vertebrate subject, e.g., shoulder, arm, wrist hand, hip, thigh, leg, ankle, or foot. For example, providing an energy stimulus to the nervous system component of the vertebrate subject can include stimulating one or more peripheral cutaneous nerves that innervate the wrist and hand and that exit the spinal cord as spinal roots C5-T2. These spinal roots traverse the brachial plexus and emerge as the peripheral nerves. The medial brachial cutaneous nerve (lesser internal cutaneous nerve; medial cutaneous nerve of arm) is distributed to the skin on the medial brachial side of the arm. The medial brachial cutaneous nerve is the smallest branch of the brachial plexus, and, arising from the medial cord, it receives its fibers from the eighth cervical and first thoracic nerves. It passes through the axilla, at first lying behind, and then medial to the axillary vein, and communicates with the intercostobrachial nerve. It descends along the medial side of the brachial artery to the middle of the arm, where it pierces the deep fascia, and is distributed to the skin of the back of the lower third of the arm, extending as far as the elbow, where some filaments are lost in the skin in front of the medial epicondyle, and others over the olecranon. It communicates with the ulnar branch of the medial antebrachial cutaneous nerve. *Gray's Anatomy: The Anatomical Basis of Clinical Practice,* 40th edition (2008), Churchill-Livingstone, Elsevier.

In further aspects, the method includes providing an energy stimulus to one or more nervous system components in combination with administering one or more immunogen to the vertebrate subject and can further include, for example, stimulating the posterior cutaneous nerve of the thigh, or posterior femoral cutaneous nerve, which innervates the skin of the posterior surface of the thigh and leg, as well as the skin of the perineum. The posterior cutaneous nerve of the thigh derives from a nerve from the sacral plexus. The posterior cutaneous nerve arises partly from the dorsal divisions of the first and second, and from the ventral divisions of the second and third sacral nerves, and issues from the pelvis through the greater sciatic foramen below the piriformis muscle. It then descends beneath the gluteus maximus with the inferior gluteal artery, and runs down the back of the thigh beneath the fascia lata, and over the long head of the biceps femoris to the back of the knee; here it pierces the deep fascia and accompanies the small saphenous vein to about the middle of the back of the leg, its terminal twigs communicating with the sural nerve. *Gray's Anatomy: The Anatomical Basis of Clinical Practice,* 40th edition (2008), Churchill-Livingstone, Elsevier.

A method for enhancing an immune response to one or more immunogen, e.g., to an infectious agent, in a vertebrate subject is described herein. The method includes providing an energy stimulus configured to modulate one or more nervous system components and administering one or more immunogen associated with the infectious agent to the vertebrate subject. A method for enhancing an immune response to one or more immunogen in a vertebrate subject in response to a neoplasm, e.g., cancer, is described herein. The method includes providing an energy stimulus configured to modulate one or more nervous system components and administering one or more immunogen associated with the neoplasm to the vertebrate subject. The energy stimulus and the one or more immunogen can be provided in one or more combinations and in one or more temporal sequences sufficient to enhance an immune response in the vertebrate subject. The method can be implemented in various combinations to provide the energy stimulus and to administer the one or more immunogen, e.g., stimulating with the energy source then immunizing with the one or more immunogen; immunizing with the one or more immunogen then stimulating with the energy source; substantially simultaneously stimulating with the energy source and immunizing with the one or more immunogen; providing an immunization booster using multiple rounds of energy stimulus and immunization with the one or more immunogens. The method that includes providing the energy stimulus and administering the one or more immunogen to the vertebrate subject can occur over a range of time periods from approximately one or more seconds, approximately one or more minutes, approximately one or more hours or approximately one or more days. Modulating the release of a neurotransmitter can include inducing or increasing the release of the neurotransmitter or inhibiting, blocking, or decreasing the release of the neurotransmitter, and can include increased or decreased production of the neurotransmitter or its genetic precursor, such as RNA.

A method is further described herein for vaccinating a vertebrate subject against a disease, the method including providing an energy stimulus configured to modulate one or more nervous system components of the vertebrate subject, and administering one or more immunogen to the vertebrate subject, wherein the energy stimulus and the one or more immunogen are provided in a combination and in a temporal sequence sufficient to enhance an immune response in the vertebrate subject. In detailed aspects, the method can be used for vaccinating a vertebrate subject to treat or prevent a disease, for example, an infectious disease, and the one or more immunogen can include all or part of a pathogen. For example, the one or more immunogens may include, but are not limited to, one or more of a bacterial antigen, a viral antigen, a fungal antigen, or a parasital antigen. In detailed aspects, the method can be used for vaccinating a vertebrate subject to treat or prevent a disease, for example one or more form of cancer, and the one or more immunogens can include, but are not limited to, one or more tumor antigen. For example the one or more immunogens can include, but are not limited to, one or more of a polypeptide, a lipid, a carbohydrate, a lipopolysaccharide, a nucleic acid, a peptide mimetic, a viral antigen, a bacterial antigen, a carcinoembryonic antigen, a mucin, a glycosphingolipid, a genetically engineered antigen, an antigen designed in silico, or a synthetic antigen. The one or more immunogens can further include, but are not limited to, one or more of Tn, STn, CEA-1, MUC-1, heat shock protein (HSP), HBV surface antigen, or PSA. See e.g., Kaufman, et al., *Transl Med.* 5: 60, 2007; Schlom, J. et al., *Clinical Cancer Research*, 13: 3776, 2007; Lewis, J. J., *Proc. Natl. Acad. Sci. USA*, 101: 14653-14656, 2004; each of which is incorporated herein by reference. In detailed aspects, the method can be used for vaccinating a vertebrate subject to treat or prevent a disease, for example one or more form of cancer caused by an infectious agent, for example, a virus, and the one or more immunogen can include all or part of the oncogenic pathogen. For example the one or more immunogen can include all or part of one or more human papilloma virus (HPV), e.g. Gardasil®, Human Papillomavirus Quadrivalent (Types 6, 11, 16, and 18) Vaccine, Recombinant, or can include all or part of one or more human T cell lymphotrophic virus (HTLV). In further aspects, the method includes enhancing an immune response in the vertebrate subject, wherein the method is configured to treat an infectious disease, a prion disease, a neoplastic disease, an amyloid disease, a heart disease, a respiratory disease, an autoimmune disease, a hyperimmune disease, or an allergic response.

In further aspects, the method includes enhancing an immune response to one or more immunogen in the vertebrate subject, wherein the method is configured to prevent an infectious disease, a prion disease, a neoplastic disease, a heart disease, a respiratory disease, an autoimmune disease, a hyperimmune disease, or an allergic response. In a method for treating or preventing an allergic response, the immunogen can include, for example, feline d1 protein or feline d1-IgG fusion protein, and the method can be used to prevent or treat an allergic response to cat dander. The immunogen can include glutaraldehyde-modified allergens, e.g., allergens for grass pollen or tree pollen, in combination with MPL and L-tyrosine to prevent or treat allergic response to grass or trees. See e.g., McCormack, et al., *Drugs*, 66: 931-938, 2006, which is incorporated herein by reference. In some aspects, the immunogen can be present on a virus-like particle (VLP), for example RNA bacteriophage Qβ, R17, fr, gA or AP205. In some aspects, the immunogen can be present on a virus-like particle (VLP), for example a plant picornavirus or cowpea mosaic virus (CPMV). In some aspects, the immunogen can be present on a virus-like particle (VLP), for example an insect nodavirus or flock house virus (FHV), for example wherein the immunogen is the VWA domain of the ANTXR2 anthrax antigen. In further aspects, the immunogen can further include a stimulatory molecule such as a cytokine, e.g., IL-15. See, e.g., Osherovich, L., *SciBX* 2(32); doi:10.1038/scibx.2009.1230; Published online Aug. 20, 2009; Koudelka, et al., *J. Virol.*, 81: 1632-1640, 2006; Manayani et al., *PLOS Pathog*, 3(10): e142. doi:10.1371/journal.ppat.0030142, October, 2007; Riley et al., *Cardiology in Review*, 16: 288-300, 2008, each of which is incorporated herein by reference.

In a method for treating or preventing a heart disease or circulatory disease, e.g., atherosclerosis, the immunogen can include oLDL, MDA-LDL, aldehyde-LDL, aldehyde-apoB100, or $CuSO_4$-LDL ($CuO_x$-LDL). In further aspects, the immunogen can include, but is not limited to, CETP HSP65 (e.g., administered orally or intranasally), HSP70, influenza vaccine, or nicotine vaccine (e.g., cyto002-NicQ(3; Cytos Biotechnology AG, Switzerland) to treat or prevent atherosclerosis. In a method for treating or preventing heart disease or circulatory disease, e.g., high blood pressure, the immunogen can include, but is not limited to, angiotensin I or angiotensin II (e.g., cyto006AngQβ; Cytos Biotechnology AG, Switzerland). See, e.g., Osherovich, L., *SciBX* 2(32); doi:10.1038/scibx.2009.1230; published online Aug. 20, 2009, which is incorporated herein by reference. In a method for treating or preventing obesity, the immunogen can include, but is not limited to, ghrelin. See, e.g., Riley et al., *Cardiology in Review*, 16: 288-300, 2008, which is incorporated herein by reference.

Methods for enhancing an immune response to one or more immunogen in a vertebrate subject include providing an energy stimulus configured to modulate one or more nervous system components and administering one or more immunogen to the vertebrate subject wherein the at least one energy stimulus and the one or more immunogen are provided in a combination and in a temporal sequence sufficient to enhance the immune response in the vertebrate subject and to treat a neoplasm in the vertebrate subject. The neoplasm can include any new or abnormal growth of tissue, wherein the tissue can be benign or malignant. The neoplasm can include a neoplasm in one or more of a lymphoid organ, thymus, spleen, bone marrow, peritoneum, mucosal tissue, or a portion of a digestive tract. The neoplasm can include a neoplasm in one or more of a myeloid tissue, a hematopoietic tissue, a nervous tissue, an epithelial tissue, an endothelial tissue, a muscle tissue, a benign tumor or a malignant tumor, a carcinoma, an adenoma, or a sarcoma. The neoplasm can include a tumor or cancer, e.g., bladder cancer, breast cancer, colon cancer, liver cancer, lung cancer, melanoma, ovarian cancer, pancreatic cancer, prostate cancer, or a papillomavirus-induced cancer. Immunogens used in the method for the treatment of neoplastic disease or cancer can include cancer antigens such as those used in cancer vaccines, e.g., heat shock protein/peptide complex (Antigenics Inc.; Oncophage), CD55, (Onyvax Limited; Onyvax-P), telomerase protein (Geron Corporation; GRN-VAC1/GNRVAC2), carbonic anhydrase IX (CA9), carcinoembryonic antigen (CEA) (Dendreon Corp), attenuated live Listeria vaccine (Advaxis, Inc.; Lovaxin C), B-cell lymphoma surface antigen (Biovest International, BiovaxID), TAP transporter protein (GeneMax Corp), E75 HER2/neu peptide (Apthera, Inc.; NeuVax).

A method is further provided wherein providing the energy stimulus includes stimulating one or more nervous system components in the vertebrate subject. In some aspects, providing the energy stimulus can excite an action potential in one or more nervous system components of the vertebrate subject. In some aspects, stimulating the nervous system component can include increasing production of one or more neurotransmitters. A method is further provided wherein providing the energy stimulus includes inhibiting one or more nervous system components in the vertebrate subject. In some aspects, providing the energy stimulus can inhibit an action potential in the one or more nervous system components of the vertebrate subject.

In the method, as provided herein, one or more neurotransmitters released by one or more nervous system components can modulate one or more nerve impulses in the vertebrate subject. In some aspects, modulating one or more nerve impulses includes, but is not limited to, inhibiting one or more nerve impulses or exciting one or more nerve impulses. In further aspects, the modulating step includes, but is not limited to, providing one or more inhibitory nerve impulses or one or more excitatory nerve impulses. In some aspects, the neurotransmitter modulates a function of one or more cells of the vertebrate subject. The one or more cells include, but are not limited to, the cell that released the neurotransmitter, a cell type that is the same as the nervous system component that released the neurotransmitter, a cell type that is a different nervous system component than the cell that released the neurotransmitter, or a cell type that is a non-nervous system component, e.g., an epidermal cell, a muscle cell, a blood cell or a lymph cell.

The method, as further provided herein, can include providing the energy stimulus to a tissue of the vertebrate subject that is in the vicinity of a lymph node. Providing the energy stimulus to the tissue in the vicinity of the lymph node can include adjacent to the lymph node or proximal to the lymph node. The method includes providing the energy stimulus to modulate one or more nervous system components that affects one or more functions of the lymph node. The tissue can be within a region of an immunogen administration site of the vertebrate subject, and the site may be near a lymph node. Tissue that is adjacent to a lymph node may be in association with the lymph node and may be in communication with the lymph node and cells therein, e.g., physically, or via biochemical means or bioelectrical means, includes tissue in association, Tissue that is adjacent to a lymph node can include, for example, nerve tissue, blood tissue, muscle tissue, epidermal tissue, or other tissue.

Methods for enhancing an immune response to one or more immunogen in a vertebrate subject can include providing an energy stimulus configured to modulate one or more nervous system components and administering one or more immunogen to the vertebrate subject in a combination and in a temporal sequence sufficient to enhance an immune response and to treat one or more inflammatory conditions, including, but not limited to, infectious diseases, e.g., viral, bacterial, parasital, and fungal infections, diseases of wound healing, HIV, influenza, or tuberculosis. The method for enhancing an immune response to one or more immunogen in a vertebrate subject can further include providing an energy stimulus configured to modulate one or more nervous system components and administering one or more immunogen to the vertebrate subject to enhance an immune response for the purpose of treating Alzheimer's disease. Immunogens provided in the method for treating AD can include antigens used in AD vaccines, e.g., β-amyloid 1-42 peptide ($A\beta_{1-42}$). See e.g., Head, et al., *J. Neourscience,* 28: 3555-3566, 2008, which is incorporated herein by reference.

A system is described herein that includes an apparatus comprising an energy generator to provide at least one energy stimulus configured to modulate one or more nervous system components of the vertebrate subject, and a device configured to administer one or more immunogen to the vertebrate subject. The system is configured to include the apparatus to provide the energy stimulus and the device to administer the one or more immunogen, in a combination and in a temporal sequence sufficient to enhance an immune response in the vertebrate subject. In detailed aspects, the energy stimulus includes one or more of electrical energy, magnetic energy, electromagnetic energy, ultrasonic energy, acoustic energy, mechanical energy, or thermal energy. In detailed aspects, the one or more immunogen includes one or more of a bacterial antigen, a viral antigen, a fungal antigen, or a parasital antigen wherein the one or more immunogen includes a tumor antigen. In further aspects, the system can include circuitry for providing an energy stimulus configured to modulate one or more nervous system components in the vertebrate subject, and circuitry for administering one or more immunogen to the vertebrate subject.

A system including a device is described herein that includes an energy generator providing an energy stimulus to modulate one or more nervous system components of a vertebrate subject and an apparatus configured to administer one or more immunogen to the vertebrate subject. In some aspects, the system including the energy generator and the apparatus to administer the immunogen delivery component can be incorporated in a single unit, or can be incorporated into two or more units, wherein the two or more units are configured to be substantially in communication. In some aspects, the system including the device can be configured to provide the energy stimulus and to administer the one or more immunogen in one or more combinations and in one or more temporal sequences sufficient to enhance an immune response, e.g., in combinations wherein the energy generator providing the energy stimulus and the apparatus configured to administer the one or more immunogen act simultaneously; wherein the energy generator provides the energy stimulus prior to the apparatus configured to administer the one or more immunogen; wherein the apparatus is configured to administer the one or more immunogen prior to the energy generator providing the energy stimulus; wherein the energy generator providing the energy stimulus and the apparatus configured to administer the one or more immunogen are utilized at one administration site; wherein the energy generator providing the energy stimulus and the apparatus configured to administer the one or more immunogen are utilized at different administration sites; wherein the energy generator providing the energy stimulus and the apparatus configured to administer the one or more immunogen are utilized in a booster immunization.

In some aspects, the apparatus configured to administer the one or more immunogens can include one or more of microneedles, microfine lances, microfine cannulas, microinjector, jet fluid injector, high pressure jet fluid injector, or tissue implant. In further aspects, the apparatus configured to administer the one or more immunogens can include one or more transdermal, transcutaneous, percutaneous, or intradermal delivery devices. The one or more transdermal delivery devices can be configured to deliver the one or more immunogens to the vertebrate subject by one or more of iontophoresis, microdialysis, ultrafiltration, electromagnetics, osmosis, electroosmosis, sonophoresis, electroporation, thermal poration, microporation, skin permeabilization, or a laser.

With reference to the figures, and with reference now to FIGS. 1, 2, 3, 4, and 5 depicted is one aspect of a device or system that may serve as an illustrative environment of and/or for subject matter technologies, for example, a device comprising an energy generator providing an energy stimulus to modulate one or more nervous system components of a vertebrate subject and an apparatus configured to deliver one or more immunogen to the vertebrate subject, or, for example, a system comprising an apparatus comprising an energy generator providing an energy stimulus to modulate one or more nervous system components of the vertebrate subject, and a device configured to deliver one or more immunogen to the vertebrate subject. Accordingly, the present application first describes certain specific methods of FIGS. 1, 2, 3, and 4; thereafter, the present application illustrates certain specific methods. Those having skill in the art will appreciate that the specific methods described herein are intended as merely illustrative of their more general counterparts.

Continuing to refer to FIG. 1, depicted is a partial diagrammatic view of an illustrative embodiment of a device 100 comprising an energy generator providing an energy stimulus to modulate one or more nervous system components of a vertebrate subject and an apparatus configured to deliver one or more immunogen to the vertebrate subject. The device 100 includes an energy generator 110 to provide energy to a surface 120 configured to provide an energy stimulus to modulate one or more nervous system components of a vertebrate subject. The device includes an apparatus including an immunogen reservoir 130 in fluid communication with a delivery interface 140, for example a microneedle or a nozzle of a microjet, configured to deliver the immunogen into a tissue, for example one or more of the epidermis, dermis, or muscle of the vertebrate subject. The delivery interface 140 delivering the one or more immunogen can be further configured as a microneedle, microjet, iontophoretic device, or patch for transcutaneous or intradermal delivery of the one or more immunogen to the vertebrate subject.

Figure 2:
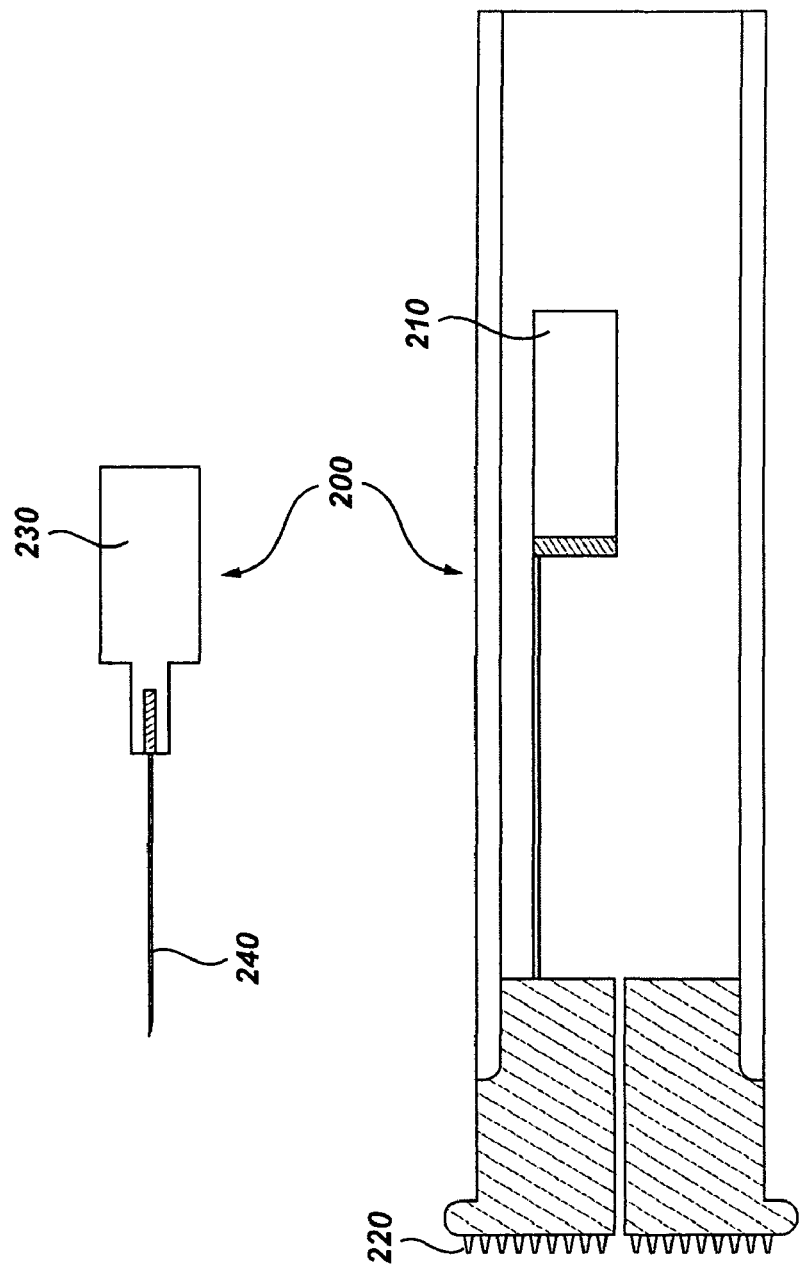
FIG. 2 depicts a diagrammatic view one aspect of an embodiment of a device configured to modulate an immune response in a vertebrate subject.

Continuing to refer to FIG. 2, depicted is a partial diagrammatic view of an illustrative embodiment of a system 200 comprising an energy generator providing an energy stimulus to modulate one or more nervous system components of a vertebrate subject and an apparatus configured to deliver one or more immunogen to the vertebrate subject. The system 200 includes an energy generator 210 to provide energy to a surface 220 configured to provide an energy stimulus to modulate one or more nervous system components of a vertebrate subject. The energy generator can include electrode pairs oriented in random, circumferential, or radial fashion. The system includes an apparatus including an immunogen reservoir 230 in fluid communication with a needle 240 configured to deliver transcutaneously or intradermally the immunogen into a tissue, for example one or more of the epidermis, dermis, or muscle of the vertebrate subject.

Figure 3:
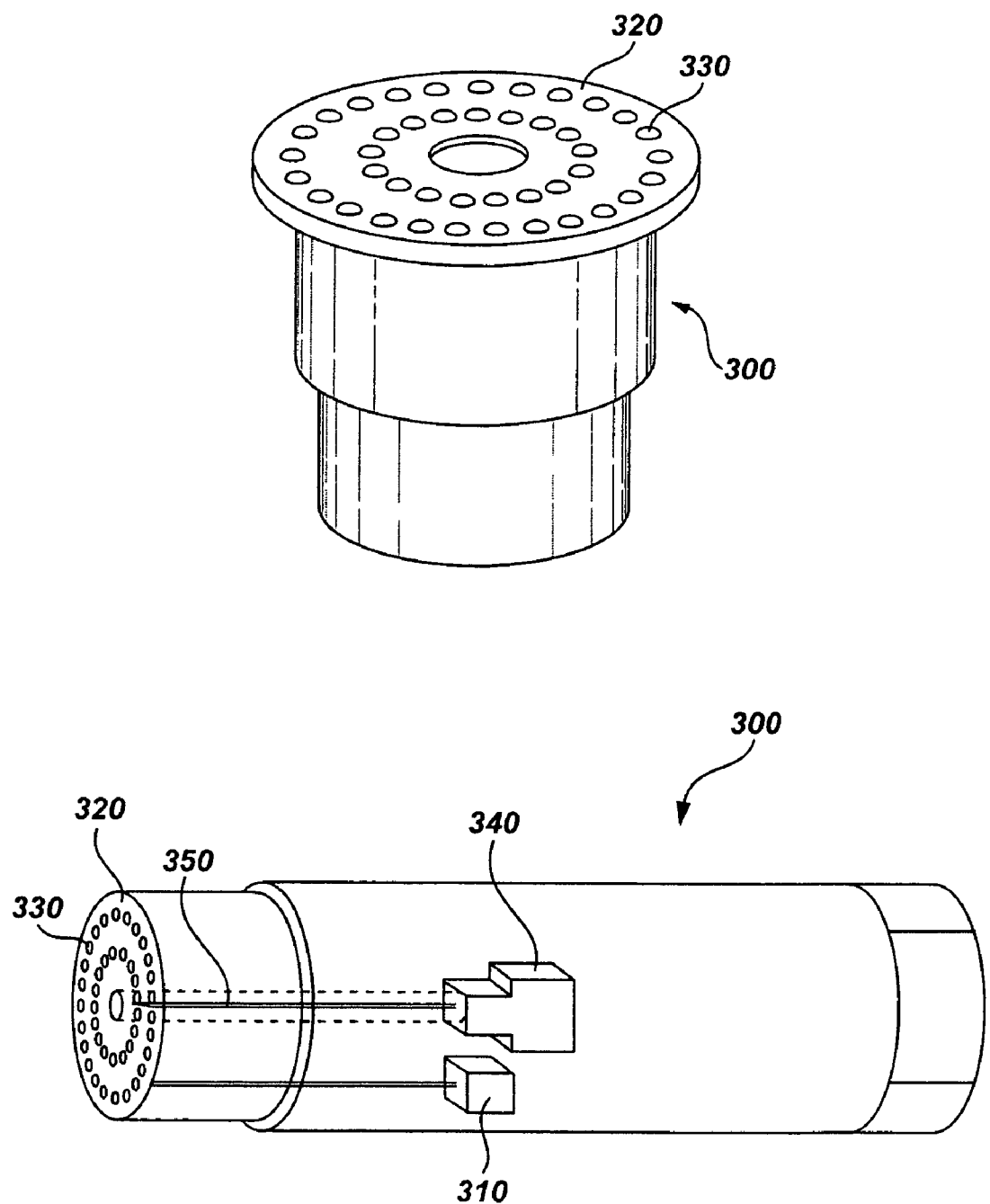
FIG. 3 depicts a diagrammatic view of one aspect of an embodiment of a device configured to modulate an immune response in a vertebrate subject.

Continuing to refer to FIG. 3, depicted is a partial diagrammatic view of an illustrative embodiment of a device 300 comprising an energy generator providing an energy stimulus to modulate one or more nervous system components of a vertebrate subject and an apparatus configured to deliver one or more immunogen to the vertebrate subject. The device 300 includes an energy generator 310 to provide energy to a surface 320 configured to provide an energy stimulus to modulate one or more nervous system components of a vertebrate subject. The device includes the surface 320 including energy contacts 330 that contact a surface, e.g., skin, of the vertebrate subject. The energy generator can include electrode pairs oriented in random, circumferential, or radial fashion. The system includes an apparatus including an immunogen reservoir 340 in fluid communication with a needle 350, e.g., a microneedle or a microjet, configured to deliver the immunogen into tissue, for example one or more of the epidermis, dermis, or muscle of the vertebrate subject. The surface 320 can retract to expose the needle, microneedle, or microjet 350 to the skin surface of the vertebrate subject.

Figure 4:
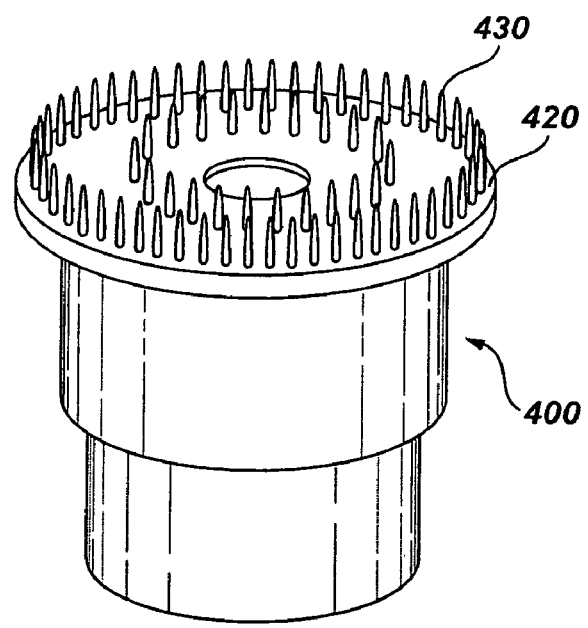
FIG. 4 depicts a diagrammatic view of one aspect of an embodiment of a device configured to modulate an immune response in a vertebrate subject.
Figure 4:
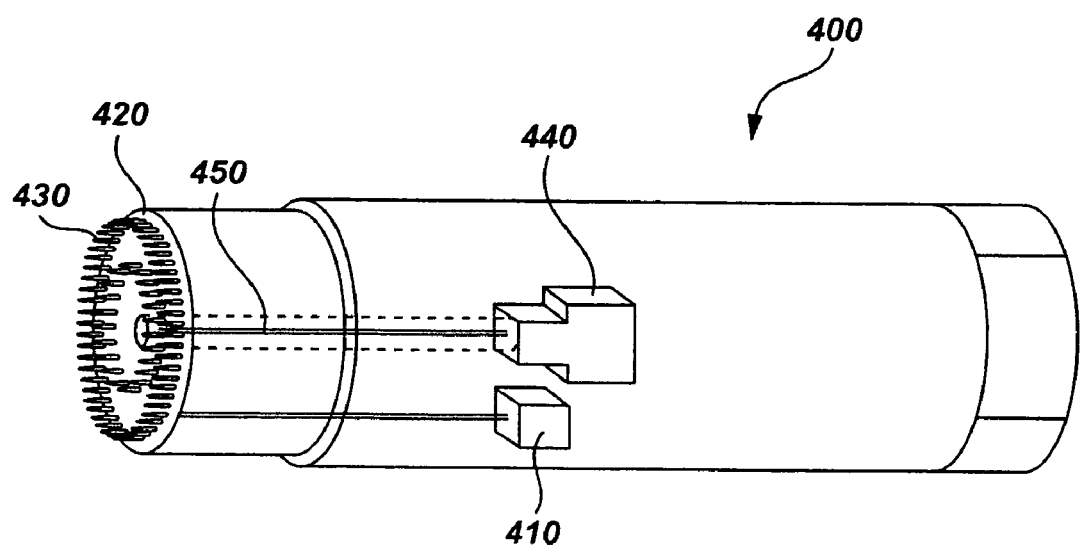

Continuing to refer to FIG. 4, depicted is a partial diagrammatic view of an illustrative embodiment of a device 400 comprising an energy generator providing an energy stimulus to modulate one or more nervous system components of a vertebrate subject and an apparatus configured to deliver one or more immunogen to the vertebrate subject. The device 400 includes an energy generator 410 to provide energy to a surface 420, the device configured to provide an energy stimulus to modulate one or more nervous system components of a vertebrate subject. The device includes the surface 420 including energy contacts 430 that contact a surface, e.g., skin, of the vertebrate subject. In some aspects, the energy contacts 430 are microneedles 430 configured to enter into the skin or into the muscle of the vertebrate subject. The microneedle is configured to provide an energy stimulus and to reduce pain upon entry of the microneedle into the skin of the vertebrate subject. The system includes an apparatus including an immunogen reservoir 440 in fluid communication with a delivery interface 450, for example, a needle, a microneedle, or a nozzle of a microjet, configured to deliver the immunogen into one or more of the epidermis, dermis, or muscle of the vertebrate subject. The device includes the surface 420 including energy contacts 430 that contact a surface, e.g., skin, of the vertebrate subject. The surface 420 can retract to expose the needle, microneedle, or microjet 450 to the skin surface of the vertebrate subject.

Figure 5:
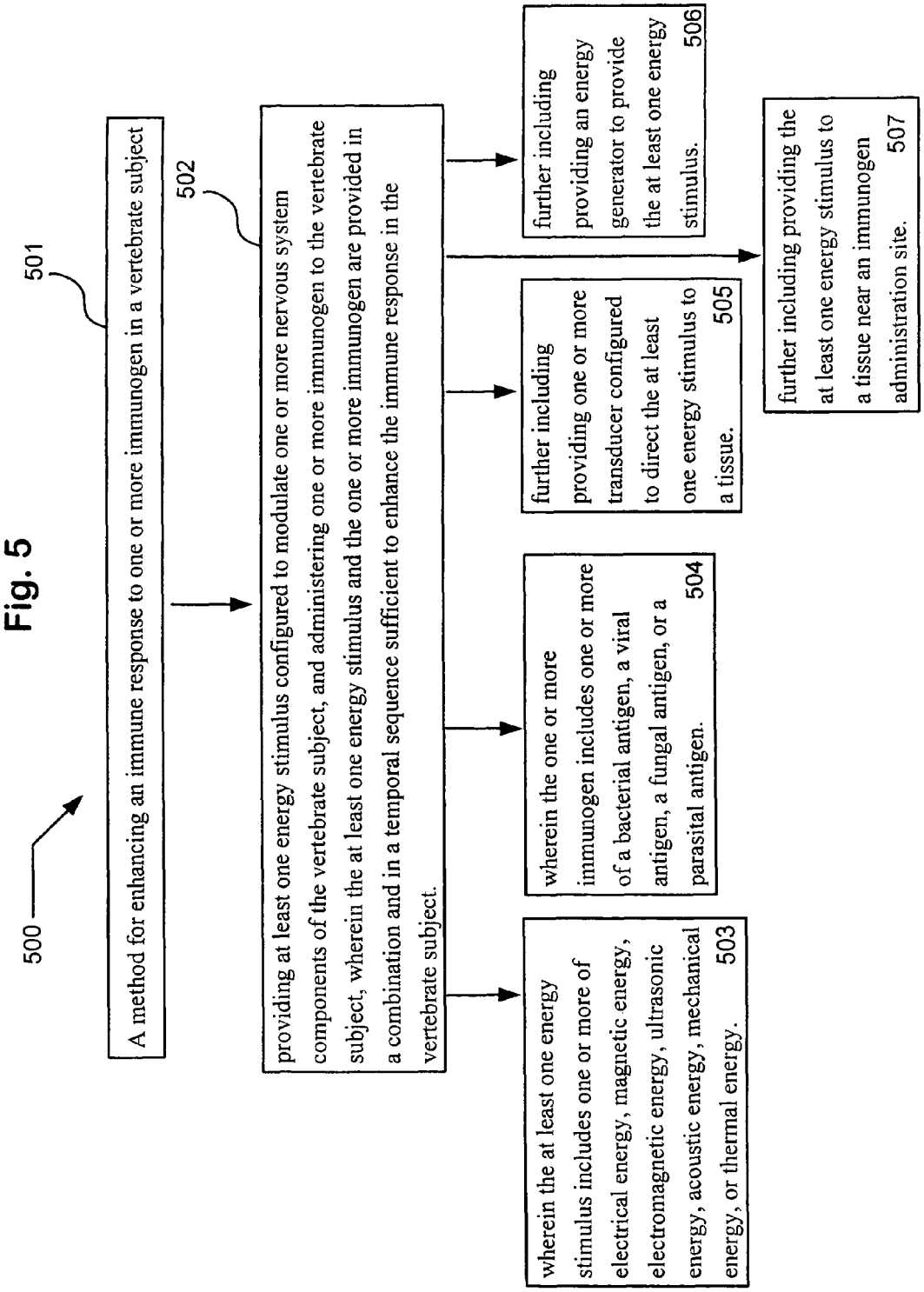
FIG. 5 illustrates a method for enhancing an immune response in a vertebrate subject.

FIG. 5 illustrates a method 500 for enhancing an immune response in a vertebrate subject. A method 501 for enhancing an immune response in a vertebrate subject includes providing 502 at least one energy stimulus configured to modulate one or more nervous system components of the vertebrate subject, and administering one or more immunogen to the vertebrate subject, wherein the at least one energy stimulus and the one or more immunogen are provided in a combination and in a temporal sequence sufficient to enhance the immune response in the vertebrate subject. The at least one energy stimulus can include 503 one or more of electrical energy, magnetic energy, electromagnetic energy, ultrasonic energy, acoustic energy, mechanical energy, or thermal energy. The one or more immunogen can include 504 one or more of a bacterial antigen, a viral antigen, a fungal antigen, or a parasital antigen. The method can further include providing 505 one or more transducer configured to direct the at least one energy stimulus to a tissue. The method can further include providing 506 an energy generator to provide the at least one energy stimulus. The method can further include providing 507 the at least one energy stimulus to a tissue near an immunogen administration site.

Electrical stimulation of one or more nervous system components at different frequencies can produce neurotransmitter release in a vertebrate subject. Animal studies have demonstrated that electrical stimulation can induce release of neurotransmitters, including neuropeptides. Neurotransmitters play important roles in various aspects of function and communication in the nervous system, and in the interaction between the nervous system and the immune system, e.g., a neurotransmitter such as a glucocorticoid, norepinephrine, noradrenalin, neuropeptide Y, or substance P, CGRP, NGF or VIP can affect an immune response in a vertebrate subject.

A system is disclosed for enhancing an immune response in a vertebrate subject includes an apparatus comprising an energy generator to provide an energy stimulus to one or more nervous system components in combination with a device configured to deliver one or more immunogen to the vertebrate subject. The system can modulate release of a neurotransmitter, for example, to elicit, enhance accelerate, prolong, facilitate, or alter in form or type an immune response in the vertebrate subject. Methods are also disclosed that utilize non-invasive strategies for providing an energy stimulus for therapeutic intervention to modulate neurotransmitter release and to treat infectious diseases or neoplastic diseases. The energy stimulus includes, but is not limited to, an electrical stimulus, magnetic stimulus, electromagnetic spectral stimulus, ultrasonic stimulus, or thermal stimulus.

In some aspects, energy stimulation of a nerve, such as electrical stimulation at specific frequencies applied to certain body sites, can facilitate the release of specific neuropeptides from one or more nervous system components, which can affect an immune response in a vertebrate subject. See, e.g., Han, *Trends in Neuroscience,* 26: 17-22, 2003; Herzberg et al., *Neuroreport.* 6: 1773-1777, 1995; "Electrical stimulation of the sciatic nerve alters neuropeptide content and lymphocyte migration in the subcutaneous tissue of the rat hind paw"; Saadé et al., *Journal of Physiology* 545.1: 241-253, 2002. "Upregulation of proinflammatory cytokines and nerve growth factor by intraplantar injection of capsaicin in rats"; and Khalil Z and Merhi M., *J Gerontol A Biol Sci Med Sci.* 55: B257-263, 2000, "Effects of aging on neurogenic vasodilator responses evoked by transcutaneous electrical nerve stimulation: relevance to wound healing", each of which is incorporated herein by reference. The target of the energy stimulation is one or more nervous system components in the vertebrate subject including, but not limited to, a central nervous system component, a peripheral nervous system component, an autonomic nervous system component, an enteric nervous system component, a vagal nerve, brain, spinal cord, a somatic nerve, a sensory nerve, a motor nerve, or a cutaneous nerve in the vertebrate subject.

In further aspects, energy stimulation of one or more nervous system components, e.g., a nerve at the skin surface, can include manual stimulation/acupuncture in combination with electrical stimulation. A system including an apparatus comprising an energy generator providing an energy stimulus to one or more nervous system components and a device configured to deliver one or more immunogens, can be configured to affect an immune response in a vertebrate subject. The energy stimulus to the nervous system component can be provided, for example, via electrodes placed on the skin (transcutaneous electrical nerve stimulation, TENS) or via a probe inserted through the skin into the tissue (percutaneous electrical nerve stimulation, PENS). If the point of stimulation is selected according to traditional acupuncture therapy, the process can be referred to as electroacupuncture (EA). Studies that compared the underlying neurobiological mechanisms of EA and TENS with acupuncture needles or skin electrodes placed at the same "acupoints" concluded that the methods operate through very similar mechanisms. See, e.g., Han, *Trends in Neuroscience,* 26: 17-22, 2003, which is incorporated herein by reference.

An energy generator providing an energy stimulus to modulate one or more nervous system components of a vertebrate subject can include a transcutaneous electrical nerve stimulation (TENS) unit consisting of 1 or more electrical-energy generators, a battery, and a set of electrodes. The TENS unit is small and programmable, and the generators can deliver trains of stimuli with variable current strengths, pulse rates, and pulse widths. The waveform is biphasic, to avoid the electrolytic and iontophoretic effects of a unidirectional current. The settings for the stimulus parameters can be, for example, 20-50 V, 1-300 ms, and 2-5 Hz for 1 minute. When TENS is used as the energy generator to provide an energy stimulus to enhance an immune response, different frequencies and intensities can be used to provide the enhanced immune response in the vertebrate subject. Optimal settings of stimulus parameters are subjective and are determined. Electrode positioning is quite important. Usually, the electrodes are initially placed on the skin in the vicinity of the injection site of the immunogen, but other locations (e.g., over cutaneous nerves, trigger points, acupuncture sites) can be used. The settings for the stimulus parameters can be, for example, 20 V at 2 millisecond, 5 Hz for 1 minute. In electroacupuncture settings, the TENS unit delivers low frequency stimulus trains, for example at 1-10 Hz at a high stimulus intensity, close to the tolerance limit of the patient. Pulsed (burst) TENS uses low-intensity stimuli firing in high-frequency bursts. The recurrent bursts discharge at, for example, 1-2 Hz, and the frequency of impulses within each burst is, for example, set at 100 Hz. The intensity of the impulse is a function of pulse duration and amplitude. The amount of output current depends on the combined impedance of the electrodes, skin, and tissues. With repetitive electrical stimuli applied to the same location on the skin, the skin impedance is reduced, that could result in greater current flow as stimulation continues. A constant current stimulator, therefore, is configured to minimize sudden, uncontrolled fluctuations of current intensity related to changes in impedance. An electroconductive gel applied between the electrode and skin can also serve to minimize the skin impedance.

Percutaneous electrical nerve stimulation (PENS) to one or more nervous system components can be used to enhance an immune response in a vertebrate subject and combines advantages of electroacupuncture and TENS for providing enhanced immune response when used in combination with providing a vaccine immunogen to the vertebrate subject. Rather than using surface electrodes, PENS uses acupuncturelike needle probes as electrodes, with these placed at dermatomal levels corresponding to local nervous system components. The main advantage of PENS over TENS is that it bypasses local skin resistance and delivers electrical stimuli at the precisely desired level in close proximity to the nervous system component, for example, when located in soft tissue, muscle, or periosteum. A number of studies have compared transcutaneous electrical nerve stimulation (TENS) with similar therapeutic modalities, including percutaneous electrical nerve stimulation (PENS), interferential current therapy (IFC), and acupuncture. See, e.g., Kaye et al., *eMedicine, Oct.* 8, 2008, which is incorporated herein by reference.

A method for enhancing an immune response to one or more immunogen in a vertebrate subject can include providing an energy stimulus to one or more nervous system components that is part of the peripheral nervous system, e.g., a cutaneous nerve, of the vertebrate subject, in combination with administering one or more immunogen to the vertebrate subject, wherein the energy stimulus and the one or more immunogen are provided in a combination and in a temporal sequence sufficient to accelerate, prolong, enhance, facilitate, or alter in form or type antigen-specific immune responses when used in combination with specific vaccine immunogens in the vertebrate subject. To stimulate a portion of the peripheral nervous system, e.g., cutaneous nerves in the vertebrate subject, a TENS device or a PENS device can be provided externally or internally wherein the stimulus, e.g., voltage or intensity, can range from about 1 millivolt to about 1 volt or more, e.g., 0.1 volt to about 50 volts, e.g., from about 0.2 volt to about 20 volts and the frequency can range from about 1 Hz to about 2500 Hz, e.g., about 1 Hz to about 1000 Hz, e.g., from about 2 Hz to about 100 Hz in certain aspects. In some aspects, a pure d-c voltages can be employed. The pulse width can range from about 1 microsecond to about 2000 microseconds or more, e.g., from about 10 microseconds to about 2000 microseconds, e.g., from about 15 microseconds to about 1000 microseconds, e.g., from about 25 microseconds to about 1000 microseconds. The electrical output can be applied for at least about 1 millisecond or more, e.g., about 1 second, e.g., about several seconds, where in some aspects the stimulation can be applied for as long as about 1 minute or more, e.g., about several minutes or more, e.g., about 30 minutes or more can be used in some aspects. See, e.g., U.S. Pat. No. 7,149,574, which is incorporated herein by reference.

The parameters for providing an energy stimulus to a vertebrate subject via an apparatus comprising an energy generator can determine the amount and type of neurotransmitter released from one or more nervous system components. For example, electroacupuncture can provide stimulation of one or more nervous system components in a vertebrate subject with low-frequency (4 Hz) stimulation and not by high-frequency (200 Hz) stimulation to result in the release of opioid neuropeptides. This release can be reversed by low doses of a neurotransmitter antagonist. Further, peripheral stimulation in the 8-100 Hz range can elevate the content of SP in rat spinal perfusate, with maximal effect at 15 Hz. Low frequency electrostimulation is sufficient to evoke efferent responses in peripheral nerves without nociception. Electrical stimulation of the sciatic nerve in rats (12 minute electrical stimulation train delivered to the right sciatic nerve; 5 msec on/off, at 10 Hz and 5-10 mV) resulted in an ipsilateral rise in substance P and a bilateral rise in VIP levels in experimental animals. Thus, different neurotransmitters are released under different conditions and can depend upon the frequency level of electrical stimulation. See, e.g., Han, *Trends in Neuroscience*, 26: 17-22, 2003; Herzberg et al., *NeuroReport* 6: 1773-1777, 1995, each of which is incorporated herein by reference.

Transcutaneous electric nerve stimulation (TENS) provides noninvasive stimulation of nerves. Low frequency electrostimulation is sufficient to evoke efferent responses in peripheral nerves without nociception. Electrostimulation of the mammalian sciatic nerve can increase levels of neuropeptides, cytokines, and other bioactive molecules, including NGF, as well as to increase blood flow and lymphocyte migration, in the cutaneous tissues of the leg ipsilateral to the stimulated nerve. See, e.g., Herzberg et al., *Neuroreport* 6(13):1773-1777, 1995; Saadé et al., *Journal of Physiology*, 545.1, pp. 241-253, 2002; and Khalil Z and Merhi M., *J Gerontol A Biol Sci Med Sci*. 55(6): B257-263, 2000, each of which is incorporated herein by reference. The effects observed with electrostimulation, including release of bioactive substances, are signs of neurogenic inflammation. The bioactive substances can include, but are not limited to, neurotransmitters, cytokines, chemokines, leukotrienes, prostaglandins, and histamine, as well as migration of leukocytes including lymphocytes. Following the immediate effects of electrostimulation, vasodilation further allows increased blood flow to the area carrying cells, including those recruited by released bioactive substances, as well as additional bioactive mediators. Binding of mediators to receptors on endothelial cells leads to further vasodilation and increased blood vessel permeability with extravasation of mediators and cells, thus providing a cascading effect. Neuropeptides released following stimulation can have specific activities to modulate an immune response. For example, neuropeptides including substance P and CGRP can have chemotactic properties for lymphocytes and immature dendritic cells (see, e.g., Dunzendorfer et al, *The J Immun.*, 166: 2167-2172, 2001; Peripheral Neuropeptides Attract Immature and Arrest Mature Blood-Derived Dendritic Cells). In addition, substance P and NGF are known to act as adjuvants (see, e.g., Herzberg et al., supra, Niizek et al., supra, U.S. Patent Applications 2005/0209625 and 2003/0099663 supra, and WO2008/088846 supra, and U.S. Pat. No. 6,572,866 Nerve growth factor as a vaccine adjuvant).

An energy stimulus by electrostimulation of sufficient strength and duration can stimulate the peripheral terminals of sensory neurons and can enhance several responses in the nearby tissues of the mammalian subject, including vasodilation, temperature increases, and release of neuropeptides and other bioactive substances. The neuropeptides and other bioactive substances can have actions toward target cells associated with a heightened immune response. Neurogenic inflammation can indicate a heightened immune response. Vasodilation allows increased blood flow carrying cells to the area. The cells can be recruited by released bioactive substances, as well as by bioactive mediators active in inflammation, such as cytokines, chemokines, leukotrienes, prostaglandins, and histamine. The binding of these mediators to their receptors on endothelial cells leads to further vasodilation and increased blood vessel permeability with extravasation of mediators and cells. Bioactive neuropeptides are also released by the stimulus of sensory nerves and include, for example, substance P. See, e.g., WO2005/094682 "Method and apparatus for electrical stimulation to enhance lancing device performance" and U.S. Application 20050209625 "Method and apparatus for electrical stimulation to enhance lancing device performance," which are incorporated herein by reference. Substance P can have chemotactic properties for lymphocytes as well as properties as an adjuvant. See Herzberg et al., Electrical stimulation of the sciatic nerve alters neuropeptide content and lymphocyte migration in the subcutaneous tissue of the rat hind paw. Neuroreport. 1995 Sep. 11; 6(13):1773-7; Niizeki et al., J. Invest. Derm. (1999) 112: 437-442; A Substance P Agonist Acts as an Adjuvant to Promote Hapten-Specific Skin Immunity; U.S. Applications 2005/0209625 and 2003/0099663 "Pharmaceutical composition comprising an antigen", and WO28088846 "Pharmaceutical composition comprising an antigen", and WO28088846 "Substance P and analogs thereof as an immunogenic composition adjuvant," each of which is incorporated herein by reference.

A system or device disclosed herein includes at least one energy generator configured to provide at least one energy stimulus, e.g., electrical stimulus utilizing one or more electrodes, to at least one nervous system component, in combination with an apparatus configured to deliver one or more immunogen to the vertebrate subject. The system or device can include the energy generator configured to provide the energy stimulus and the apparatus configured to deliver the one or more immunogen in a combination and in a temporal sequence sufficient to enhance an immune response in response to one or more immunogen in the vertebrate subject. The electrodes can be positioned in an array on the cap to form one or more electrode sets. See, e.g., FIGS. 1 through 4. The one or more electrode sets can be deployed on the cap in a variety of electrode arrays. They can be positioned in a random fashion with pairs positioned adjacent one another without any specific orientation. Alternatively, the pairs can be arranged in circumferential fashion around the cap. A further orientation can include radial arrays. The random orientation of the electrodes can stimulate one or more nervous system components to affect an immune response in the vertebrate subject. In other aspects, the electrodes can be oriented other than in the random fashion and still achieve the device providing neural modulation. An example of a device configured to provide electrical pulses to stimulate peripheral sensory neurons in a vertebrate subject can be found, for example, in WO 2005/094682, which is incorporated herein by reference.

The electrodes can be connected by leads to an energy generator and controller. The energy generator is supplied with electrical power from a power source such as a battery via leads. The energy generator comprises an integrated circuit (IC) oscillator having input leads. The oscillator provides an output on a terminal via a resistor to the gate of a transistor. The transistor can be connected between leads on the input to a step up transformer. An output terminal of the oscillator provides an input to a variable resistor so as to control the frequency of oscillator. The output side of transformer is connected to output leads that lead to the electrodes. Capacitors provide smoothing of the output wave. The transistor acts to pass current through the input side of transformer in approximately a square wave. The transformer increases the voltage output to an equivalent square wave on the output side. A capacitor smoothes the wave form so that it is a high voltage waveform having a frequency, amplitude, or duration, e.g., an alternating current (AC) waveform. A variable resistor is adjustable by means of an operator-manipulated knob via an appropriate connection.

The energy generator can be of a type that generates a high voltage AC wave. The voltage level can be approximately from 10 to 25 kilovolts. In some aspects, the frequency is 20 Hz. In a further aspect, the energy generator can provide a constant voltage stimuli of 1 to 5 V, at 2 ms and 1 Hz, for 10 minutes before delivering the one or more immunogens and for 10 minutes after delivering the one or more immunogens, configured to enhance an immune response to one or more immunogen in a vertebrate subject. The energy generator controller can be adapted to control the energy generator through a range of frequencies, voltages and at low current (i.e., 100 milliamps) as appropriate for the applications described herein.

The device can be useful in a method for enhancing an immune response to one or more immunogen in a vertebrate subject. The device includes an energy generator to provide an energy stimulus configured to modulate one or more nervous system components in combination with one or more immunogen provided to the vertebrate subject wherein the energy stimulus and the one or more immunogen are provided in a combination and in a temporal sequence sufficient to accelerate, prolong, enhance, facilitate, or alter in form or type antigen-specific immune responses when used in combination with specific vaccine antigens in the vertebrate subject. Methods for enhancing an antigen-specific immune response in a vertebrate subject, when used in combination with specific vaccine antigens, can include an adjuvant effect to enhance, accelerate, prolong, facilitate, or alter in form or type the immune response to the one or more antigens in the vertebrate subject.

The temporal pattern of administration can include providing the energy stimulus configured to modulate one or more nervous system components of the subject, followed by administering one or more immunogen, e.g., a vaccine including a pharmaceutical composition including one or more immunogen, wherein the energy stimulus and the one or more immunogen are provided in a combination and in a temporal sequence sufficient to accelerate, prolong, enhance, facilitate, or alter in form or type antigen-specific immune responses when used in combination with specific vaccine antigens in the vertebrate subject. In a further aspect, the one or more energy stimuli can be provided over several days, for example once or twice per day for 10 to 30 minutes for 5 days, and the one or more immunogen provided after the last stimulus, for example 60 minutes after the last stimulus. The one or more energy stimuli can be provided over a range of time periods from approximately one or more seconds, approximately one or more minutes, approximately one or more hours or approximately one or more days. In further aspects, the temporal pattern of administration can include administering a vaccine including a pharmaceutical composition including one or more immunogen, followed by providing the energy stimulus configured to modulate one or more nervous system components of the subject, in a manner sufficient to enhance the immune response in the vertebrate subject. In further aspects, the temporal pattern of administration can include a vaccine including a pharmaceutical composition including one or more immunogen administered simultaneously with providing the energy stimulus configured to modulate one or more nervous system components of the subject, in a manner sufficient to enhance the immune response in the vertebrate subject.

In some aspects, the energy generator provides electrical pulses to stimulate the peripheral terminals of sensory neurons in the body, which causes the release of bioactive substances including neurotransmitters. These bioactive substances include, but are not limited to, NGF, cytokines, and neuropeptides such as substance P (SP) and calcitonin gene-related peptide (CGRP). These bioactive substances in turn act on target cells in the periphery of the applied area such as mast cells, immune cells and smooth muscle cells producing neurogenic inflammation. Neurogenic inflammation can be characterized by redness and warmth in the treated area that is an indication of vasodilation.

In order for electrical stimulation to be used to enhance an immune response to one or more immunogen in a vertebrate subject, the electrical stimulation pulse can be applied for a duration prior to or following vaccination of the vertebrate subject with a vaccine immunogen. The electrical power can be applied through the one or more electrode pairs, or it can be embodied in the device having a flat-faced skin-contacting cap with a plurality of electrode pairs positioned to generally surround a central point on the cap. The cap is connected to a housing containing the elements as described above. The electrode pairs can be oriented in random, circumferential, or radial fashion. See e.g., FIGS. 1 through 4.

Methods for enhancing an immune response to one or more immunogens in the vertebrate subject can be achieved with electrical stimulation within a range of intensities. Neurogenic inflammation can be induced by electrical stimulation. The one or more electrical stimulation can be provided, for example, at 20 Hz for 60 seconds prior to providing a vaccine immunogen to the vertebrate subject. In a further aspect, the one or more electrical stimulation can be provided over several days, for example, once or twice per day for 10 to 30 minutes for 5 days, and the one or more immunogen provided after the last stimulus, for example, 60 minutes after the last stimulus. The one or more energy stimuli can be provided over a range of time periods from approximately one or more seconds, approximately one or more minutes, approximately one or more hours or approximately one or more days. In further aspects, a method for enhancing an immune response including neurogenic inflammation in the vertebrate subject can be achieved when the electrical stimulation can be applied for a duration of approximately 30 to 60 seconds, or approximately 60 seconds and above. The electrical stimulation can be at 16-20 kilovolts alternating current, and approximately 20 Hz. A method including electrical stimulation prior to or following vaccination with a vaccine immunogen can be continued periodically over several minutes, hours, or days, to enhance an immune response to one or more immunogens in the vertebrate subject.

In some aspects, a device or a system includes an energy generator configured to provide an energy stimulus to at least one nervous system component, e.g., efferent vagus nerve fibers, in combination with an apparatus configured to deliver one or more immunogen to the vertebrate subject. The energy stimulus can include, but is not limited to, one or more of an electrical stimulus, a magnetic stimulus, electromagnetic stimulus, ultrasonic stimulus, acoustic stimulus, mechanical stimulus, or thermal stimulus. Nonlimiting examples of the energy stimulus include: mechanical stimulus such as a needle or acupuncture, ultrasound, or vibration; electromagnetic radiation such as infrared, visible or ultraviolet light; heat, or any other energy source. In some aspects, the vagus nerve is stimulated electrically, for example, using a vagus nerve stimulator such as the Cyberonics NCP® electric probe. In further aspects, the vagus nerve is stimulated electrically, for example, using a SAINT™ microtransponder for wireless RFID neurostimulation. MicroTransponder, Dallas, Tex. The SAINT™ microtransponder unit eliminates any implantable battery or wires. The microtransponder is injectable with a 12-gauge needle in a 30 minute outpatient procedure. This implanted microtransponder can be coupled to an external controller, that can be worn like an armband; and will provide the power and stimulus parameters for the device. The external controller will be able to interface with a PDA or computing device in order to change the stimulus parameters to better treat the patient's profile.

In an aspect, the nervous system component, e.g., efferent vagus nerve, can be stimulated by stimulating the entire vagus nerve (e.g., both the afferent and efferent nerves), or by isolating efferent nerves and stimulating them directly. The latter method can be accomplished by separating the afferent from the efferent fibers in an area of the nerve where both types of fibers are present. Alternatively, the efferent fiber is stimulated where no afferent fibers are present, for example, close to the target organ served by the efferent fibers. The efferent fibers can also be stimulated by stimulating the target organ directly, e.g., electrically, thus stimulating the efferent fibers that serve that organ. In other aspects, the ganglion or post-ganglionic neurons of the vagus nerve can be stimulated. In an experimental setting, the vagus nerve can also be cut and the distal end can be stimulated, thus only stimulating efferent vagus nerve fibers. In an aspect, stimulating or inhibiting the nervous system component can modulate afferent nerves. For example, a nervous system component of the afferent nervous system can be inhibited thus inhibiting an inflammatory response. For example, a nervous system component of the afferent nervous system can be stimulated to signal a major nerve branch such that the major nerve can provide signaling downstream to stimulate an immune tissue or immune cell.

In some aspects, an ultrasound stimulus can be applied in a noninvasive manner to modulate the activity of one or more nervous system components in combination with administering one or more immunogen to the vertebrate subject in a method for enhancing an immune response in a vertebrate subject. Ultrasound as an energy stimulus can replace invasive techniques that use implanted electrodes for the stimulation of one or more nervous system components. Ultrasonic stimulus can be a useful modality for noninvasive stimulation due to its ability to precisely and flexibly control the parameters, and because it can be safer than other stimulation methods in clinical applications. Ultrasonic stimulus can be used to provide an energy stimulus configured to modulate one or more nervous system components, in combination with administering one or more immunogen to the vertebrate subject, wherein the energy stimulus and the one or more immunogen are provided in a combination and in a temporal sequence sufficient to enhance the immune response in the vertebrate subject.

In further aspects, the device includes an energy generator including one or more ultrasound transducers and a controller. The one or more ultrasound transducer can be positioned to direct an ultrasound signal toward one or more nervous system components. Nervous system components can be stimulated using ultrasound signal. In some aspects, the ultrasound stimulation mechanically stimulates the nervous system component through displacement of the medium. The ultrasonic stimulus can also heat the tissue, that may also contribute to neural stimulation. The device further includes an apparatus configured to deliver one or more immunogen to the vertebrate subject, and can be used to enhance an immune response in a vertebrate subject. The controller is configured to deliver an electrical signal to the one or more ultrasound transducer to generate the ultrasonic stimulus in a temporal pattern and at variable energy levels toward the nervous system component. In further aspects, the controller is configured to control a phase of the electrical signal to each of the one or more ultrasound transducer to cause resulting ultrasonic stimulus from the one or more ultrasound transducer to constructively interfere at the nervous system component and provide sufficient energy to stimulate the nervous system component. See, e.g., U.S. 2007/0191906 Method And Apparatus For Selective Nerve Stimulation; Tsui et al., *Ultrasonics* 43: 560-565, 2005; and Tyler, et al. 2008 Remote Excitation of Neuronal Circuits Using Low-Intensity, Low-Frequency Ultrasound. PLoS ONE 3(10): e3511. doi:10.1371/journal.pone.0003511, each of which is incorporated herein by reference.

In some aspects, the device including the energy generator can use at least two ultrasonic crystals to focus the energy, and further aspects of the energy generator can use at least three crystals to focus the energy. The energy from each crystal may not be individually high enough to stimulate the nerve, but the combination of crystals is capable of stimulating the nerve when the energy wave from multiple ultrasonic crystals constructively interfere. In some aspects, the energy generator can direct ultrasonic energy to stimulate selective nerves. For example, the device can provide stimulation waveforms toward the nervous system component using transducers located at various radial positions with respect to an imaginary axis that passes through the nervous system component. Positioning the two or more transducers at radial positions with relatively wide angles, such as greater than or equal to 45 degrees, the ultrasonic energy waves are able to be focused with greater accuracy and selectivity. Additional selectivity can be achieved using three or more transducers radially positioned about the imaginary axis passing through one or more nervous system components. Each transducer produces a waveform with an energy, such that only a constructive interference of all waveforms at the focal point provides sufficient stimulation energy greater than a threshold to stimulate the nervous system component. The focal point of the energy beams can be adjusted to selectively stimulate parts of a nerve bundle. For example, the focal point can be changed by changing the phase of the energy, by physically adjusting the position or orientation of the ultrasonic crystals, or a combination of physically adjusting the orientation of the ultrasonic crystals or the phase of the energy. Various ultrasonic waveforms can be used. In a square waveform, for example, a pulse width and amplitude can be adjusted to minimize stimulation of surrounding fiber populations, and a duty cycle can be varied to increase or decrease rate of stimulation. An appropriate feedback signal that reflects a desired or undesired response can be used to determine whether the energy has been focused on a desired nerve bundle. Selective stimulation of the nervous system component can be achieved without penetrating the nerve, without relatively complex stimulation waveforms, and without steering currents.

The pulse width and pulse amplitude of the ultrasonic waveform can be adjusted to minimize stimulation of surrounding nerve fiber populations and the duty-cycle can be increased or decreased to alter the rate of stimulation. Different sized nerve fibers within the same bundle (e.g., motor neurons or sensory neurons) can be stimulated selectively to create individual effects. The device can be used for vagal nerve stimulation in combination with an apparatus configured to deliver one or more immunogen to the vertebrate subject to enhance an immune response in the vertebrate subject. Since physical contact with the target nerve is not necessary, the transducers can be positioned using a nerve cuff to surround only the nerve, or can be positioned to surround a larger, more stable structure such as the nerve and an adjacent vessel, or can be externally positioned. Examples of externally-positioned transducers include transducers placed around a neck of the vertebrate subject to stimulate a nerve such as a vagus nerve, or transducers placed around a limb to stimulate a corresponding nerve in the limb. Such transducers can be incorporated in collars, bracelets, or patches, for example, for use in stimulating the neck, arm or leg of the vertebrate subject. A desired fiber can be stimulated, regardless of the specific geometry and makeup of the nerve.

In some aspects, the device including an ultrasound transducer can use piezoelectric crystals to focus ultrasound energy to an adjustable focal point. The piezoelectric element provides a mechanical movement in response to an electrical signal. Examples of piezoelectric elements include quartz crystal and polarized ferroelectrics, both of which have electric dipoles in their construction that realign under the presence of an applied voltage, causing the element to reshape. The device can further include a matching layer to mimic the properties of the tissue, to reduce or eliminate energy reflections, and a backing layer to reduce vibration and echoes.

Various aspects of the device can include external ultrasonic transducers to selectively stimulate one or more nervous system components with ultrasonic energy waves from the external transducers. For example, a number of external placement devices, such as bracelets, belts or collars, can be used. For example, a wearable device can include one or more transducers configured to direct ultrasonic energy toward a neural target. See, e.g., US 2007/0191906, which is incorporated herein by reference.

In further aspects, a device or a system including an energy generator providing an energy stimulus, e.g., a magnetic stimulus, to modulate one or more nervous system components of a vertebrate subject and an apparatus configured to deliver one or more immunogen to the vertebrate subject can be used in a method for enhancing an immune response in the vertebrate subject. Neuromagnetic stimulation is a magnetic stimulus to modulate one or more nervous system components that can be useful for noninvasive stimulation, due to an ability to precisely and flexibly control the parameters of the stimulation. The device or system can include an energy generator to provide neuromagnetic stimulation configured to modulate one or more nervous system components of the vertebrate subject, in combination with administering one or more immunogen to the vertebrate subject, wherein the energy stimulus and the one or more immunogen are provided in a combination and in a temporal sequence sufficient to enhance the immune response in the vertebrate subject. For example, a device can include one or more transducers configured to direct transcutaneous magnetic stimulation toward a neural target including, but not limited to a brain, a cranial nerve, or a trigeminal nerve of the vertebrate subject. See, e.g., U.S. Patent Applications 2008/0306326, 2008/0306325, 2006/0094924, each of which is incorporated herein by reference.

In some aspects, a device is described that includes an energy generator to stimulate one or more nervous system components by neuromagnetic stimulus in combination with ultrasonic stimulus, and further administering one or more immunogen to a vertebrate subject, wherein the neuromagnetic stimulus in combination with ultrasonic stimulus and the one or more immunogen are provided in a combination and in a temporal sequence sufficient to enhance the immune response in the vertebrate subject. In detailed aspects, since tissue is conductive, particle motion created by an ultrasonic wave can induce an electric current density generated by Lorentz forces. An electric field distribution can be induced by a collimated ultrasonic beam. For example, peak electric fields of up to 8 V/m appear to be achievable at the upper range of diagnostic intensities. This field strength is about an order of magnitude lower than fields typically associated with neuromagnetic stimulation. The electric field gradients induced by ultrasound can be high (about 60 kV/m2 at 4 MHz), which may theoretically play a more important role in activation than the field magnitude. The latter value is comparable to neuromagnetic induction gradients. See, e.g., Norton, Biomed Eng Online, 2: 6, 2003; U.S. Patent Application 2007/0255085; each of which is incorporated herein by reference. In another aspect, ultrasonic stimulus has an ability to noninvasively propagate through bone and other tissues in a focused manner. Low-intensity, low-frequency ultrasound (LILFU) is capable of remotely and noninvasively exciting neurons and network activity. See e.g., Tyler et al., Remote Excitation of Neuronal Circuits Using Low-Intensity, Low-Frequency Ultrasound. *PLoSONE*, 3(10): e3511.doi:10.1371/journal.pone.0003511, 2008, which is incorporated herein by reference.

In some aspects, the device can be used for a method for enhancing an immune response in a vertebrate subject to locally stimulate one or more nervous system components by inducing an electric field in regions where the neuromagnetic stimulus in combination with the ultrasonic stimulus is focused. In an aspect, the device can include an energy generator including an ultrasonic source that emits, using phase and amplitude control, focused ultrasonic waves, by an array of ultrasound emitters into a region of the tissue, including, but not limited to, nerves of an intradermal region, nerves of a subcutaneous region, nerves of one or more regions within the body that can focus, e.g., on the sciatic nerve. For example, a subcutaneous region of tissue can be targeted such that the device including the energy generator produces a subcutaneous ultrasound focus (region) approximately 1 cm in diameter orthogonal to the z axis of the main direction of radiation. This can readily be accomplished in the frequency range 0.2 to 3.0 MHz, and is particularly easy in the frequency range of about 0.3 to 0.5 MHz. If the power density $P_{us}$ in the focal region is sufficiently high, the tissue particles vibrate at the ultrasound frequency. Ionized particles within the nerve tissue and, particularly, electrons are therefore mobilized, that corresponds to an alternating current J. Simultaneous application of a magnetic field with an induction B orthogonal to the direction of vibration or current J will produce a so-called Lorentzian force F orthogonal to B and J; this B-field can be a DC-magnetic field or a pulsed magnetic field. The simultaneous interaction of a constant B-field and focused ultrasound can lead to an accumulation of negative charges in the region x>0, and an equally large accumulation of positive charges in the region x<0. The simultaneous interaction of a constant B-field and focused ultrasound can provide a resulting voltage 2 V between the two charged regions.

In an aspect, a device is described that includes an energy generator configured to stimulate one or more nervous system components by ultrasonic stimulus in combination with neuromagnetic stimulus, and further in combination with administering one or more immunogen to a vertebrate subject. The mechanism of stimulation utilizes the superposition of electric currents introduced by the following electric field sources induced by the ultrasonic stimulus in combination with neuromagnetic stimulus: (1) Hall Effect due to the interaction of ultrasound and magnetic fields; (2) Magnetic induction of electric current due to oscillating magnetic fields, as is the case with coil electrodes or by transcranial magnetic stimulation (TMS); and (3) Transcutaneous Electrical Neural Stimulation (TENS) devices. The techniques described above can be used in principle to stimulate any type of excitable tissue, including, for example, cortical tissue, central nervous tissue, and peripheral nerve tissue, to enhance an immune response in a vertebrate subject. See, e.g., Norton, *Biomed Eng Online,* 2: 6, 2003; U.S. 2007/0255085; which is incorporated herein by reference.

In some aspects, a system including a device including an energy generator providing an energy stimulus to modulate one or more nervous system components of a vertebrate subject and an apparatus configured to deliver one or more immunogen to the vertebrate subject, can include one or more aspects of the system which can be implanted into the vertebrate subject. The implantable system can include one or more of a device including an energy generator, an apparatus, and a controller regulating the energy generator configured to provide the energy stimulus.

For example, the implantable system can include an implantable controller containing an induction coil for inductive electrical coupling to a coil of an external controller configured to provide the energy stimulus to modulate one or more nervous system components, e.g., vagus nerve, of the vertebrate subject. The implantable controller can further regulate injection and release of the one or more immunogen into an epidermal layer, dermal layer, or muscle layer of the vertebrate subject. The energy stimulus and the one or more immunogen are provided in a combination and in a temporal sequence sufficient to enhance the immune response in the vertebrate subject. The implantable controller can include anterior and posterior pulse generators electrically connected through conductors to anterior and posterior pacing electrodes, e.g., for attachment to anterior and posterior trunks, respectively, of the vagus nerve. The implantable controller can also include a battery and a CPU that includes program storage and memory. The timing and parameters of the pulse at the electrodes can be adjusted by inductively coupling the external controller to the implantable controller and inputting pacing parameters, e.g., pulse width, frequency and amplitude.

In some aspects, a system including a fully implantable controller is desirable. In further aspects, the electrodes can be implanted and connected to a receiving antenna placed near the body surface. The control circuits can be housed in an external pack worn by the patient with a transmitting antenna held in place on the skin over the area of the implanted receiving antenna. Such a design is forward-compatible in that the implanted electrodes can be later substituted with the implantable controller at a later surgery if desired. The controller can also include circuits generating nerve conduction block signals that connect to electrodes that can be positioned on the nerve proximally, distally, or both.

In some aspects, the device can include implantable transducers, e.g., electrical transducers implanted subcutaneously, intramuscularly, or intravenously. The device can be shaped as a cuff to surround and target one or more nervous system components. In further aspects, the transducers can be powered by and be in communication with an implantable device. The devices can include transducers with power circuitry and communication circuitry for self-powering its own stimulation, and coordinating the stimulation with other transducers for a desired therapy. In some aspects, the electrical transducers can be included in an implanted device. The implanted device functions as a base, and the electrical transducers function as satellites wirelessly linked to the base. Power and data can be sent over the wireless link using, for example, radio frequency or ultrasound technology. Examples of satellite transducers include subcutaneous transducers, nerve cuff transducers and intravascular transducers. See, e.g., U.S. Pat. No. 7,321,793, and U.S. Patent Application 2005/0143787, each of which is incorporated herein by reference.

In some aspects, the system including a device including an energy generator and an apparatus configured to deliver one or more immunogen to the vertebrate subject can be micronized and, optionally, injectable. See, e.g., U.S. 2009/0157147 *Implantable Transponder Systems and Methods* by L. Cauller and R. Weine, and U.S. 2008/0319506, *Grooved electrode and wireless microtransponder system*, by L. Cauller, each of which is incorporated herein by reference. A system configured to accelerate, prolong, enhance, facilitate, or alter in form or type antigen-specific immune responses when used in combination with specific vaccine antigens in a vertebrate subject can also include an energy generator, e.g., one that includes an energy source such as a battery or generator, where in some aspects the energy source can be implantable and can also include one or more leads or wires for coupling the one or more electrodes to an energy source. In some aspects, a power source can be separate from or external to the energy source, e.g., in an external controller, and provide energy wirelessly. See, e.g., U.S. 2005/0143787, "Method and system for providing electrical pulses for neuromodulation of vagus nerve(s), using rechargeable implanted pulse generator", U.S. 2009/0157147, and U.S. 2008/0319506, each of which is incorporated herein by reference. In some aspects, the system can include one or more nervous system pharmacological agents, for example in combination with the one or more immunogen. In some aspects, suitable delivery means can be included, according to the particular pharmacological agent, e.g., the particular formulation of the agent such as formulation into preparations in solid, semi-solid, liquid or gaseous forms, e.g., tablets, capsules, powders, granules, ointments, solutions, suppositories, injections, inhalants and aerosols, and the particular mode of administration of the agent, e.g., oral, buccal, rectal, parenteral, intranasal, intrapulmonary, intradermal, transdermal, or intracheal. Accordingly, certain systems can include a suppository applicator, syringe, IV bag and tubing, in combination with one or more, energy generator components. Systems can also include one or more apparatuses for delivering, e.g., implanting, an electrosurgical apparatus to a target site of a subject such as into the body cavity of a subject. For example, an endoscope or introducer needle can be provided. See, e.g. U.S. 2009/0157147 and U.S. Pat. No. 7,444,183, each of which is incorporated herein by reference. Systems can also include one or more imaging or scanning apparatuses such as a fluoroscope, or CT scan. See, e.g., U.S. Pat. No. 7,149,574, which is incorporated herein by reference.

In an aspect, a device for enhancing an immune response in a vertebrate subject including an energy generator providing an energy stimulus to modulate one or more nervous system components of a vertebrate subject and an apparatus configured to deliver one or more immunogen to the vertebrate subject, can further include a suitable detector for detecting one or more physical and/or chemical aspects, for example, those related to the function of the nervous system. The detector can include a data gathering module. The device can respond to the data gathering module by altering the energy stimulus or vaccine delivery of the immunogen to the vertebrate subject. A data analysis module can be provided wherein the data analysis module can be a separate component from or integral with the data gathering module, but in many aspects is operatively coupled to, e.g., integral with, the data gathering module. For example, data related to one or more aspects of the nervous system component can be collected by the data gathering module and forwarded to the data analysis module that executes steps necessary to process and evaluate the collected data and determine whether the nervous system component is in need of energy stimulation. Such evaluation can include comparing data to reference values. When present, a detector (or data evaluation module) can be operatively coupled to one or more other elements of a device including an energy generator such that results of the determinations of, for example, a nervous system stimulus can automatically trigger (or cease) activation of an energy stimulus to the nervous system component. Accordingly, the device including an energy generator can be activated to provide the appropriate energy stimulus. Suitable detectors include any detector capable of gathering information about the nervous system and include both invasive, minimally invasive, and non-invasive detectors where in some aspects a detector can be an implantable detector. Suitable detectors include, but are not limited to, those capable of collecting data regarding nerve conduction, neurotransmitter levels, circulating catecholamine levels, heart rate variability ("HRV"), post-ganglionic action potentials, or QT interval, and include, but are not limited to, MR1 apparatus, CT apparatus, neurography apparatus, cardiovascular monitor, or sensor including electrodes.

A system or device for enhancing an immune response to one or more immunogen in a vertebrate subject, can include circuitry for an energy generator providing an energy stimulus to modulate one or more nervous system components of a vertebrate subject, and circuitry for an apparatus configured to deliver one or more immunogen to the vertebrate subject. In some aspects, the system or device for enhancing an immune response in a vertebrate subject can include recordable-type computer readable media and programming stored thereon. For example, the system or device for enhancing an immune response in a vertebrate subject can include a suitable computing module such as suitable hardware/software for performing one or more aspects of the method for enhancing an immune response. For example, one or more aspects of the system or device can be in the form of computer readable media having programming stored thereon for implementing the methods for enhancing an immune response. Accordingly, programming in the system or device can be recorded on computer-readable media, e.g., any medium that can be read and accessed directly or indirectly by a computer. Such media include, but are not limited to, recordable-type media including computer disk or CD, a floppy disc, a magnetic "hard card", a server, magnetic tape, optical storage such as CD-ROM and DVD, electrical storage media such as RAM and ROM, and the hybrids of these categories such as magnetic/optical storage media. One of skill in the art can readily appreciate how any of the presently known computer readable media can be used to provide a manufacture that includes a recording of the present programming/algorithm for carrying out the above-described methodology. Thus, the computer readable media can be, for example, in the form of any of the above-described media or any other computer readable media capable of containing programming, stored electronically, magnetically, optically or by other means. As such, stored programming embodying steps for carrying-out methods for enhancing an immune response in a vertebrate subject can be transferred to a computer-operated apparatus such as a personal computer (PC) or personal digital device (PDD), by physical transfer of a flash drive, CD, floppy disk, or like medium, or can be transferred using a computer network, server, or other interface connection, e.g., the internet. See, e.g., U.S. Pat. No. 7,149,574, which is incorporated herein by reference.

In an aspect, the system or device for enhancing an immune response in a vertebrate subject can further include a computer readable medium that includes stored programming embodying an algorithm for carrying out some or all of the methods for enhancing an immune response, where such an algorithm is used to direct a processor or series of processors to execute the steps necessary to perform the task(s) required of it and in some aspects the system or device includes a computer-based system for carrying-out some or all of the methods for enhancing an immune response. For example, such a stored algorithm can be configured to, or otherwise be capable of, directing a microprocessor to receive information directly or indirectly from data gathering module (i.e., information collected by data gathering module about the nervous system) and process that information to determine the state of an immune response and the need for delivery of immunogen to the vertebrate subject, and the state of one or more nervous system components in the vertebrate subject, e.g., the activity level of the nervous system component and even whether the nervous system component requires modulation, and the specifics of the modulation that is required. The result of that processing can be communicated to a user, e.g., via audio and/or visual means, e.g., the algorithm can also include steps or functions for generating a variety of nervous system component profile graphs or plots.

The algorithm can be configured to, or otherwise be capable of, directing a microprocessor to activate, i.e., turn "on" and "off" a system or device for applying an energy stimulus to at least a part of one or more nervous system components and an apparatus configured to deliver one or more immunogen to the vertebrate subject, e.g., in response to the above-described determination of the state of the nervous system. For example, if it is determined that nervous system activity needs to be increased or decreased, the processor can direct the system or device to provide the appropriate energy to result in the desired action. Accordingly, a processor can select the appropriate parameters (e.g., frequency, or amplitude) depending on what is required and direct the system device to implement the parameters.

The system or device can also include a data set of known or reference information stored on a computer readable medium to which nervous system data collected can be compared for use in determining the state of the nervous system. The data can be stored or configured in a variety of arrangements known to those of skill in the art. See, e.g., U.S. Pat. No. 7,149,574, which is incorporated herein by reference.

Kits. Also provided are kits including a system or device for practicing the method for enhancing an immune response in a vertebrate subject. While the kits may vary greatly in regards to the components included, typically, the kits at least include an energy generator, e.g., that provides one or more of an electrical stimulus, a magnetic stimulus, electromagnetic stimulus, ultrasonic stimulus, acoustic stimulus, mechanical stimulus, or thermal stimulus, as described above. Accordingly, kits can at least include an electrostimulatory device such that they include at least one energy generator, e.g., one or more electrode for electrically modifying at least a portion of one or more nervous system components of the vertebrate subject, and an apparatus configured to deliver one or more immunogen to the vertebrate subject, in accordance with the systems, devices, and methods as described herein. In some aspects, the device provided in a kit is an implantable device, or at least certain components such as one or more electrodes, are implantable. Certain kits can include a plurality of electrodes, where some or all may be the same, or some or all may be different. For example, certain kits can include at least a first electrode for electrically stimulating at least a first portion of the nervous system component and at least a second electrode for inhibiting activity in at least a second portion of the nervous system component. Still further, one or more electrodes can be included in a kit that, instead of or in addition to delivering electric impulses to at least a portion of the nervous system component, delivers one or more immunogen to the vertebrate subject. Kits typically also include an energy source such as a battery or generator, where in some aspects the energy source can be implantable, and can also include one or more leads or wires for coupling the one or more electrodes to an energy source.

Kits including one or more systems or devices for delivering, e.g., implanting, an electrosurgical device to a target site of a subject such as into the body cavity of a subject can also be included in the kits. For example, an endoscope, or introducer needle can be provided.

The kits also generally include instructions for how to practice the methods for enhancing an immune response and in particular how to use the system or device provided in the kit to treat a subject for a condition, including infectious disease or neoplastic disease, by energy modulation of at least a portion of the nervous system component in combination with an apparatus configured to deliver one or more immunogen to the vertebrate subject. The instructions are generally recorded on a suitable recording medium or substrate. For example, the instructions can be printed on a substrate, such as paper or plastic, etc. As such, the instructions can be present in the kits as a package insert, in the labeling of the container of the kit or components thereof (i.e., associated with the packaging or sub-packaging) etc. In other aspects, the instructions are present as an electronic storage data file present on a suitable computer readable storage medium, e.g. CD-ROM, diskette, etc. In yet other aspects, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

The kits can further include an energy generator in combination with one or more immunogens, wherein the energy stimulus and the one or more immunogen are provided in a combination and in a temporal sequence sufficient to elicit an immune response in the vertebrate subject. The dosage amount of the one or more immunogen provided in a kit may be sufficient for a single application or for multiple applications. Accordingly, in some aspects of the kits a single dosage amount of one or more immunogen is present. In certain other aspects, multiple dosage amounts of the one or more immunogens or the pharmacological agent can be present in a kit. In those aspects having multiple dosage amounts of pharmacological agent, such can be packaged in a single container, e.g., a single tube, bottle, or vial, or one or more dosage amounts can be individually packaged such that certain kits can have more than one container of the one or more immunogens or the pharmacological agent.

Suitable means for delivering the one or more immunogens or the one or more pharmacological agents to a subject can also be provided in a subject kit. The particular delivery means provided in a kit is dictated by the particular immunogens or pharmacological agent employed, as described above, e.g., the particular form of the agent such as whether the one or more immunogens or the pharmacological agent is formulated into preparations in solid, semi-solid, liquid or gaseous forms, such as tablets, capsules, powders, granules, ointments, solutions, suppositories, injections, inhalants or aerosols, and the particular mode of administration of the agent, e.g., whether oral, buccal, rectal, parenteral, peritoneal, intradermal, transdermal, intracheal, etc. Accordingly, certain systems can include a suppository applicator, syringe, IV bag and tubing, electrode.

Some or all components of the kits can be packaged in suitable packaging to maintain sterility. In some aspects of the kits, the components of the kit are packaged in a kit containment element to make a single, easily handled unit, where the kit containment element, e.g., box or analogous structure, may or may not be an airtight container, e.g., to further preserve the sterility of some or all of the components of the kit. See, e.g., U.S. Pat. No. 7,149,574, which is incorporated herein by reference.

It is evident from the above discussion that the above described invention provides methods, devices, system and kits for vaccinating a vertebrate subject to prevent or ameliorate a disease or condition or effects thereof, including an infectious disease or a neoplastic disease, that are simple to use, effective, and can be used in therapy for a variety of different diseases or conditions.

The methods and compositions are further described with reference to the following examples; however, it is to be understood that the methods and compositions are not limited to such examples.

PROPHETIC EXAMPLES

Example 1

Immunization Strategy for Enhancing an Immune Response Against a Virus in a Human Subject Including Pre-Stimulation of a Nerve Site A method for enhancing an immune response can be used in a human subject to prevent infection with an influenza virus. Influenza viruses inducing illness in humans are members of the orthomyxovirus family and include influenza viruses A, B and C. Influenza A viruses, which are among the most common, are divided into subtypes based on two surface proteins, hemagglutinin (H) and the neuraminidase (N). There are 16 different known hemagglutinin subtypes and 9 different neuraminidase subtypes. Influenza A viruses can be further broken down into different strains. Strains of influenza A (H1N1) and A (H3N2) have circulated widely in human populations since 1977 and are included in yearly vaccines. In April 2009, an antigenically distinct, novel influenza A (H1N1) was identified, and infection quickly reached pandemic proportions.

In a method for enhancing an immune response in a human subject against an influenza A strain, for example an H1N1 strain, an energy stimulus configured to modulate a nervous system component of the vertebrate subject is provided at the skin surface near a site chosen for immunization, i.e. the immunization site. In some cases, the immunization site is chosen for its location near one or more lymph nodes, for example in the arm near the brachial axillary lymph nodes. An energy stimulus that is an electrical stimulus is provided by an apparatus having a plurality of electrodes in contact with the skin, for example surrounding the immunization site. The apparatus provides a stimulus of 10 to 25 kilovolts at low current for 30 seconds. An energy stimulus of this strength and duration stimulates the peripheral terminals of sensory neurons and to enhance several responses in the nearby tissues, including vasodilation, temperature increases, and release of neuropeptides and other bioactive substances, which have actions toward target cells associated with the immune response. Vasodilation allows increased blood flow to the area carrying cells as well as bioactive mediators active in inflammation, such as cytokines, chemokines, leukotrienes, prostaglandins, and histamine. The binding of these mediators to their receptors on endothelial cells leads to further vasodilation and increased blood vessel permeability with extravasation of mediators and cells. Bioactive neuropeptides are also released by the stimulus of sensory nerves and include, for example, substance P. Substance P can have chemotactic properties for lymphocytes as well as properties as an adjuvant.

After a 30 second electrical stimulation of 10 to 25 kilovolts at low current on the skin surrounding the immunization site, the tissue exhibits the above phenomena indicative of increased immune responses. One or more immunogen is provided to the subject. The immunogen includes a preparation of influenza immunogen, for example an inactivated, split-virion preparation of an influenza A (H1N1) strain that includes a concentration of HA protein in the range of 5-50 micrograms, for example, 9 micrograms. The immunogen preparation is intradermally administered substantially at the immunization site. Intradermal administration is performed using a microinjection system, such as the Becton-Dickinson Soluvia™ Prefillable Microinjection System (Becton, Dickinson and Company, Franklin Lakes, N.J.). The use of such a preparation and microinjection system are described in Beran et al., *BMC Med* 2009 Apr. 2; 7:13, 2009; "Intradermal influenza vaccination of healthy adults using a new microinjection system: a 3-year randomised controlled safety and immunogenicity trial" or Holland et al., *J Infect Dis.* 2008 Sep. 1; 198(5): 650-8.658, 2008; "Intradermal Influenza Vaccine Administered Using a New Microinjection System Produces Superior Immunogenicity in Elderly Adults: A Randomized Controlled Trial"; Laurent P, et al., *Vaccine*, 25: 8833-8842, 2007; and Laurent P, et al., *Vaccine*, 25: 6423-6430, 2007, each of which is incorporated herein by reference. Intradermal injection of a viral antigen allows exposure to local immune response machinery, now enhanced by the neurogenic inflammation. Intradermal vaccination allows for the capture and transport of antigen by dendritic cells in the dermis to the draining lymph nodes, as well as the direct migration of free antigen through the lymph ducts to the nodes, where it is captured by lymph node resident dendritic cells. In addition, antigens that migrate outwards to the epidermis are likely captured by Langerhan's cells. The neuropeptides, neurotransmitters, and other mediators associated with the neurogenic inflammation affect these immune cells and their microenvironment. See, e.g. Dunzendorfer et al., *The J Immun*, 2001, 166:2167-2172; Peripheral Neuropeptides Attract Immature and Arrest Mature Blood-Derived Dendritic Cells and Steinhoff, et al., *Arch Dermatol.* 2003; 139:1479-1488. Modern Aspects of Cutaneous Neurogenic Inflammation, which is incorporated herein by reference. In some cases, the formulation of the immunogen includes one or more strains of influenza virus, for example, three strains of influenza virus presented as a trivalent vaccine, a commonly used strategy for seasonal strains. The formulation of the immunogen includes in some cases, additional compounds, for example a polycationic substrate. Polycationic substrates have immunostimulatory effects that are increased when used with neuroactive compounds including substance P (see, e.g., U.S. Pat. No. 7,244,438 Uses for polycationic compounds and U.S. Application 2003/0099663, each of which is incorporated herein by reference).

Example 2

Immunization Strategy for Enhancing an Immune Response Against a Varicella-Zoster Virus in a Human Subject Including Stimulation of a Peripheral Nerve A method for enhancing an immune response is used in a human subject to prevent or modulate infection with or reactivation of Varicella-Zoster Virus (VZV) and accompanying afflictions. Varicella-Zoster Virus (also known as Herpes Zoster Virus or Human Herpes Virus-3) is a highly infectious virus that causes Varicella (chicken pox), usually in childhood. A vaccine prepared from live, attenuated VZV is commercially available under the name Varivax® varicella virus vaccine live (Merck & Co., Inc., Whitehouse Station, N.J.) and is claimed to be >94% effective against primary Varicella infection in healthy children. However, in children with HIV there is a decreased immune response following vaccination as compared to reported values for healthy children. After the infectious period, VZV can migrate to sensory nerve roots and remain dormant throughout life. Under stress or with immune suppression, the latent virus may be reactivated and migrate to the skin. Reactivation of latent VZV results in shingles, or Herpes Zoster, which presents as a dermatomal rash with pox-like lesions. A vaccine to prevent reactivation, comprising live attenuated VZV and marketed under the name Zostavax® zoster vaccine live (Merck & Co., Whitehouse Station, N.J.), is approved for use in individuals over the age of 60 and is under study for use in individuals with HIV (see, e.g. Oxman, M.D., et al., N Engl J Med 2005; 352:2271-84. "A Vaccine to Prevent Herpes Zoster and Postherpetic Neuralgia in Older Adults"; Gershon, et al., Pedia Infect Dis J; 2009 28:7, pp 653-655 "A Phase I-II Study of Live Attenuated Varicella-Zoster Virus Vaccine To Boost Immunity in Human Immunodeficiency Virus-Infected Children With Previous Varicella"; and "Live Zoster Vaccine in HIV-Infected Adults on Antiretroviral Therapy"— NCT00851786-80204 Clinical Trial 317018 Permalink: http://www.ClinicalConnection.com/exp/ExpandedSubjectViewStudy317018.aspx). This vaccine acts as a booster on the immune memory, which suppresses replication of the virus and protects from reactivation.

In a method for enhancing an immune response in a human subject to prevent reactivation of VZV and Zoster onset and to reduce the risk of accompanying afflictions such as postherpetic neuralgia, an energy stimulus configured to modulate a nervous system component of the vertebrate subject is provided to a peripheral nerve. Transcutaneous electric nerve stimulation (TENS) is used. Low frequency electrostimulation is sufficient to evoke efferent responses in peripheral nerves without nociception.

In the method for enhancing an immune response to reduce the potential for reactivation of VSV and Herpes Zoster in a human subject, the sciatic nerve of the human subject would be stimulated with a TENS unit using parameters of 20-50 V, 1-300 ms, and 2-5 Hz for 1 to 60 minutes. In an example, the right sciatic nerve in the mid-thigh region of a subject would be stimulated with a TENS unit using the parameters 20 V, 2 ms, and 5 Hz for 1 min (see, e.g., Khalil and Merhi 2000 supra and WIPO WO/2005/014105 "Nerve function and tissue healing"). Varivax® varicella virus vaccine live antigen or Zostavax® zoster vaccine live is administered within 60 minutes, as described herein. In some subjects, for example, elderly non-responders or individuals infected with HIV, the stimulation is repeated twice per day for 5 days, and a single immunogen administration is provided on the fifth day, 30-60 minutes after the TENS stimulation. Skin vascular reactivity induced by sensory nerves and neurogenic inflammatory reactions in general can decline with age or disease. Daily stimulation with low frequency TENS can enhance declining nerve response and increase vascular reactivity (see e.g., Kalil and Merhi 2000, supra and WO/2005/014105 supra). Alternatively or instead, burst TENS is provided to a peripheral nerve, either to the sciatic nerve or, for example in an obese subject, to the saphenous nerve, with parameters of 300 ms and 2 Hz for 30 min (see, e.g., Burssens, et al., Acta Orthopcedica Belgica, 2003, 69, 528-532 Influence of burst TENS stimulation on the healing of Achilles tendon suture in man), each day for 1 or 5 days, and antigen administration provided 30-60 minutes after the last TENS stimulation.

In a method for enhancing an immune response in a human subject to prevent reactivation of VZV and Zoster and reduce the risk of accompanying afflictions such as postherpetic neuralgia, stimulation of a peripheral nerve would be followed by antigen administration of live, attenuated VZV. For example, 45 minutes after the stimulation of the subject's right sciatic nerve, the subject is given a subcutaneous injection in the right thigh of a suspension containing not less than 19,400 plaque-forming units [PFU] of the Oka/Merck strain of VZV (a formulation obtainable under the commercial name Zostavax® zoster vaccine live), or an equivalent immunization preparation. Injection in the right thigh places the immunogen in the vicinity of the inguinal lymph nodes. A method of enhancing an immune response to an antigen administered to a leg has the added benefit (especially if the subject is a thin elderly person) of utilizing a larger, more dense area of tissue, including subcutaneous tissue. In another example, an obese subject is treated with burst TENS of the left saphenous nerve, using the parameters above. A subcutaneous injection of antigen is given in the posterior calf, several inches below the knee and near the popliteal lymph nodes found in the knee.

In addition, the method described herein is used for enhancing an immune response in a human subject to reduce the potential for primary or recurrent infection with VZV and Varicella. For example, an individual infected with HIV and at risk for Varicella infection is fit with a TENS unit, for example around the upper right arm, and a peripheral nerve, for example the median nerve. The nerve is stimulated using the parameters 20 V, 2 ms, and 5 Hz for 1 min. After 45 minutes, a subcutaneous injection is administered to the upper arm, of a 0.5 mL solution containing a minimum of 1350 PFU of Oka/Merck VZV (available from Merck under the name Varivax® varicella virus vaccine live), or an equivalent immunogen. Alternatively, the antigen administration may take place prior to or concurrent with the nerve stimulation.

In some cases, as part of the method for enhancing an immune response in a human subject to prevent infection with or reactivation of VZV and VZV-related afflictions, response of the subject to the TENS stimulation in combination with VZV immunogen vaccine would be examined and the method modified as necessary. For example, any of the treated human subjects would be tested, for example six weeks, six months, 1 year, and yearly, for antibody titers and cell-mediated responses to VZV, and the utilized strategy considered and modified. For example, if after being treated as above, the 75 year old female is found to have mounted a strong response, no additional action would be taken. On the other hand, if her cell-mediated immune response at 6 weeks is found to be low, the method would be repeated using increased TENS stimulation times, for example two TENS stimulations per day for 5 days, and 45 minutes after the last stimulation, the Zostervax® zoster vaccine live vaccine would be administered.

Example 3

Immunization Strategy for Enhancing an Immune Response in a Human Subject Including Vaccination with a Tumor Antigen Followed by Electrical Stimulation Block to a Vagal Nerve An immunization strategy is designed for prevention, modulation, or treatment of cancer in a human subject. The immunization strategy provides an enhanced immune response to one or more immunogen, e.g., an immunogen associated with pancreatic cancer. The immunization includes administration of a pharmaceutical composition including carcinoembryonic antigen (CEA) and MUC-1.

A human subject presenting with metastatic pancreatic cancer is given a subcutaneous injection with a pharmaceutical composition including a vaccinia virus vector expressing tumor antigens CEA and MUC-1. See, e.g., Kaufman, et al., Transl Med. 5: 60, 2007. Poxvirus-based vaccine therapy for patients with advanced pancreatic cancer, each of which is incorporated herein by reference. Subsequently, the human subject is treated with an intraluminal electrode apparatus applied via the esophagus. Such an apparatus is configured to provide an electrical signal of a type selected to generate a blocking signal to a vagal nerve situated external to the alimentary tract. See, e.g. U.S. Pat. No. 7,444,183 "Intraluminal electrode apparatus and method", which is incorporated herein by reference. Acetylcholine, the principal vagus nerve neurotransmitter, inhibits cytokine release from resident tissue macrophages, termed the "cholinergic antiinflammatory pathway." Vagotomy can decrease or eliminate an anti-inflammatory response; functionally, a vagal nerve block is a reversible vagotomy. Following injection with the vaccine, the human subject is treated with the vagal nerve block over a period of time, for example, once daily for 30 days, thus allowing the temporary inhibition of the cholinergic pathway, for example, in the vicinity of the pancreas. The block parameters of the apparatus (signal type and timing) are able to be altered by a controller and can further be coordinated with pacing signals of a pacing electrode for additional modulation of the vagal nerve. A representative blocking signal is a 500 Hz signal using an alternating current or a direct current (e.g., −70 mV DC). The electrical blocking stimulus provided to the human subject is configured to modulate the vagal nerve at a level and for a time sufficient to provide an adjuvant effect to the immune response to the tumor antigen, CEA and/or MUC-1, in the human subject. Following vaccination with CEA tumor antigen in combination with electrical stimulation, the antibody titer and T cell-mediated immune response are increased in human subjects compared to human subjects receiving CEA tumor antigen vaccination alone.

Each disclosed range of values of dosages or stimulus signal includes all combinations and sub-combinations of range values, as well as specific numerals contained therein.

All publications and patent applications cited in this specification are herein incorporated by reference to the extent not inconsistent with the description herein and for all purposes as if each individual publication or patent application were specifically and individually indicated to be incorporated by reference for all purposes.

The state of the art has progressed to the point where there is little distinction left between hardware and software implementations of aspects of systems; the use of hardware or software is generally (but not always, in that in certain contexts the choice between hardware and software can become significant) a design choice representing cost vs. efficiency tradeoffs. There are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Optical aspects of implementations will typically employ optically-oriented hardware, software, and or firmware.

In a general sense the various aspects described herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). The subject matter described herein may be implemented in an analog or digital fashion or some combination thereof.

The herein described components (e.g., steps), devices, and objects and the description accompanying them are used as examples for the sake of conceptual clarity and that various configuration modifications using the disclosure provided herein are within the skill of those in the art. Consequently, as used herein, the specific examples set forth and the accompanying description are intended to be representative of their more general classes. In general, use of any specific example herein is also intended to be representative of its class, and the non-inclusion of such specific components (e.g., steps), devices, and objects herein should not be taken as indicating that limitation is desired.

With respect to the use of substantially any plural or singular terms herein, the reader can translate from the plural to the singular or from the singular to the plural as is appropriate to the context or application. The various singular/plural permutations are not expressly set forth herein for sake of clarity.

The herein described subject matter sometimes illustrates different components contained within, or connected with, different other components. It is to be understood that such depicted architectures are merely examples, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality, and any two components capable of being so associated can also be viewed as being "operably couplable," to each other to achieve the desired functionality. Specific examples of operably couplable include but are not limited to physically mateable or physically interacting components or wirelessly interactable or wirelessly interacting components or logically interacting or logically interactable components.

While particular aspects of the present subject matter described herein have been shown and described, changes and modifications may be made without departing from the subject matter described herein and its broader aspects and, therefore, the appended claims are to encompass within their scope all such changes and modifications as are within the true spirit and scope of the subject matter described herein. Furthermore, it is to be understood that the invention is defined by the appended claims. It will be understood that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an"; the same holds true for the use of definite articles used to introduce claim recitations. In addition, even if a specific number of an introduced claim recitation is explicitly recited, such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, or A, B, and C together, etc.). Virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

While various aspects and embodiments have been disclosed herein, other aspects and embodiments will be apparent to those skilled in the art after reading the disclosure herein. The various aspects and embodiments disclosed herein are for purposes of illustration and are not intended to be limiting, with the true scope and spirit being indicated by the following claims.

What is claimed is:

1. A device comprising:
an energy generator configured to provide at least one energy stimulus, one or more transducer configured to direct the at least one energy stimulus to one or more nervous system components in a tissue of a vertebrate subject, and an apparatus configured to deliver one or more immunogen to the vertebrate subject, wherein the at least one energy stimulus and the one or more immunogen are configured to elicit an enhanced immune response to a disease in the vertebrate subject.

2. The device of claim 1, wherein the energy generator provides the at least one energy stimulus and the apparatus is configured to deliver the one or more immunogen, wherein the at least one energy stimulus and the one or more immunogen are configured in a combination and in a temporal sequence sufficient to enhance the immune response to the disease in the vertebrate subject.

3. The device of claim 2, wherein the apparatus further includes one or more reservoirs including at least one of the one or more immunogen or one or more adjuvants.

4. The device of claim 1, wherein the at least one energy stimulus includes one or more of electrical energy, magnetic energy, electromagnetic energy, ultrasonic energy, acoustic energy, mechanical energy, or thermal energy.

5. The device of claim 4, wherein the at least one energy stimulus includes an electrical stimulus in combination with an ultrasonic stimulus.

6. The device of claim 4, wherein the at least one energy stimulus includes an electrical stimulus in combination with a magnetic stimulus.

7. The device of claim 4, wherein the at least one energy stimulus includes an electrical stimulus in combination with a mechanical stimulus.

8. The device of claim 1, wherein the at least one energy stimulus includes at least one energy characteristic having one or more of waveform, frequency, amplitude, or duration.

9. The device of claim 1, further including circuitry configured to provide the at least one energy stimulus in a temporal sequence configured to modulate one or more nervous system components in the vertebrate subject, and to provide the one or more immunogen to the vertebrate subject.

10. The device of claim 1, wherein the one or more immunogen includes one or more of a bacterial antigen, a viral antigen, a fungal antigen, or a parasital antigen.

11. The device of claim 1, wherein the one or more immunogen includes a tumor antigen.

12. The device of claim 1, wherein the one or more immunogen includes one or more of a polypeptide, a lipid, a carbohydrate, a lipopolysaccharide, a peptide mimetic, a viral antigen, a bacterial antigen, a carcinoembryonic antigen, a mucin, a glycosphingolipid, a genetically engineered antigen, an antigen designed in silico, or a synthetic antigen.

13. The device of claim 1, wherein the energy generator providing the at least one energy stimulus and the apparatus configured to deliver the one or more immunogen is provided simultaneously.

14. The device of claim 1, comprising one or more controllers configured to activate the energy generator to deliver the at least one energy stimulus prior to activating the apparatus to deliver the one or more immunogen.

15. The device of claim 1, comprising one or more controllers configured to activate the apparatus to deliver the one or more immunogen prior to activating the energy generator to deliver the at least one energy stimulus.

16. The device of claim 1, wherein the energy generator providing the at least one energy stimulus and the apparatus configured to deliver the one or more immunogen are provided at one administration site.

17. The device of claim 1, wherein the energy generator providing the at least one energy stimulus and the apparatus configured to deliver the one or more immunogen are provided at different administration sites.

18. The device of claim 1, wherein the energy generator providing the at least one energy stimulus and the apparatus configured to deliver the one or more immunogen are provided as multiple rounds of immunization with the at least one energy stimulus and the one or more immunogen.

19. The device of claim 1, wherein the energy generator and the apparatus are enclosed in a single unit.

20. The device of claim 1, wherein the energy generator and the apparatus are enclosed in two or more units, wherein the two or more units are configured to be substantially in communication.

21. The device of claim 1, wherein the energy generator includes one or more transducer configured to direct the at least one energy stimulus.

22. The device of claim 1, wherein the at least one energy stimulus includes an excitatory stimulus directed to the one or more nervous system components.

23. The device of claim 1, wherein the at least one energy stimulus includes an inhibitory stimulus directed to the one or more nervous system components.

24. The device of claim 1, wherein the at least one energy stimulus is configured to modulate release of a neurotransmitter.

25. The device of claim 24, wherein the neurotransmitter is configured to provoke an excitatory nerve impulse in the vertebrate subject.

26. The device of claim 24, wherein the neurotransmitter is configured to provoke an inhibitory nerve impulse in the vertebrate subject.

27. The device of claim 24, wherein the neurotransmitter includes a glucocorticoid, norepinephrine, noradrenalin, neuropeptide Y, substance P, CGRP, NGF or VIP.

28. The device of claim 24, wherein the at least one energy stimulus is provided to the vertebrate subject within a region of an immunogen administration site in the vertebrate subject.

29. The device of claim 28, wherein the at least one energy stimulus is provided to the vertebrate subject in a location configured to stimulate a lymph node within the region of the immunogen administration site.

30. The device of claim 28, wherein the at least one energy stimulus is configured to stimulate a lymphoid organ, thymus, spleen, bone marrow, peritoneum, mucosal tissue, or a portion of a digestive tract of the vertebrate subject.

31. The device of claim 1, wherein the at least one energy stimulus is configured to elicit a systemic neurogenic response in the vertebrate subject.

32. The device of claim 1, wherein the at least one energy stimulus is configured to elicit a local neurogenic response in the vertebrate subject.

33. The device of claim 32, wherein the at least one energy stimulus is provided in an application pattern including at least one energy characteristic having one or more of waveform, frequency, amplitude, or duration, to elicit the neurogenic response in the vertebrate subject.

34. The device of claim 33, wherein the application pattern includes a cyclical pattern, an intermittent pattern, a repetitive pattern, a random pattern, or a non-random pattern.

35. The device of claim 1, wherein the apparatus configured to deliver the one or more immunogen includes one or more of microneedles, microfine lances, microfine cannulas, microinjector, jet fluid injector, high pressure jet fluid injector, or tissue implant.

36. The device of claim 1, wherein the apparatus configured to deliver the one or more immunogen includes one or more of transdermal delivery devices, transcutaneous delivery devices, percutaneous delivery devices, intradermal delivery devices, or implantable delivery devices.

37. The device of claim 1, wherein at least a portion of the energy generator configured to deliver the at least one energy stimulus is implantable.

38. The device of claim 1, wherein the energy generator configured to deliver the at least one energy stimulus is configured to deliver the at least one energy stimulus to the one or more nervous system components of the vertebrate subject from a site external to the vertebrate subject.

* * * * *